US008178349B2

(12) United States Patent
Terskikh et al.

(10) Patent No.: US 8,178,349 B2
(45) Date of Patent: May 15, 2012

(54) HOMOGENEOUS NEURAL PRECURSOR CELLS

(75) Inventors: Alexy Terskikh, La Jolla, CA (US); Ruchi Bajpai, La Jolla, CA (US)

(73) Assignee: Burnham Institute For Medical Research, La Jolla, CA (US)

( * ) Notice: Subject to any disclaimer, the term of this patent is extended or adjusted under 35 U.S.C. 154(b) by 355 days.

(21) Appl. No.: 11/815,786

(22) PCT Filed: Feb. 9, 2006

(86) PCT No.: PCT/US2006/004957
§ 371 (c)(1),
(2), (4) Date: Aug. 8, 2007

(87) PCT Pub. No.: WO2006/086746
PCT Pub. Date: Aug. 17, 2006

(65) Prior Publication Data
US 2008/0254004 A1    Oct. 16, 2008

Related U.S. Application Data

(60) Provisional application No. 60/651,932, filed on Feb. 9, 2005.

(51) Int. Cl.
*C12N 5/0735* (2010.01)
*C12N 5/0797* (2010.01)

(52) U.S. Cl. .................... 435/377; 435/325; 435/368
(58) Field of Classification Search .................. 435/325, 435/368, 377
See application file for complete search history.

(56) References Cited

U.S. PATENT DOCUMENTS

| | | | |
|---|---|---|---|
| 6,613,568 | B2 | 9/2003 | Kaufman et al. |
| 6,833,269 | B2 | 12/2004 | Carpenter et al. |
| 2002/0068045 | A1* | 6/2002 | Reubinoff et al. ........... 424/93.7 |
| 2002/0164308 | A1 | 11/2002 | Reubinoff et al. |
| 2003/0068819 | A1 | 4/2003 | Zhang et al. |
| 2004/0014210 | A1 | 1/2004 | Jessel et al. |
| 2006/0211109 | A1* | 9/2006 | Totey et al. ........... 435/366 |

FOREIGN PATENT DOCUMENTS

| | | |
|---|---|---|
| WO | WO 01/68815 A1 | 9/2001 |
| WO | WO 2004/029203 A2 | 4/2004 |
| WO | WO 2004029203 A2 * | 4/2004 |
| WO | 2004081172 | 9/2004 |

OTHER PUBLICATIONS

Itskovitz-Eldor et al. Differentiation of Human Embryonic Stem Cells into Embryoid Bodies Comprising the Three Embryonic Germ Layers. Molecular Medicine 6(2): 88-95, 2000.*
Zhang et al. In vitro differentiation of transplantable neural precursors from human embryonic stem cells. Nat Biotechnol. Dec. 2001;19(12):1129-33.*
Sauer et al. Role of reactive oxygen species and phosphatidylinositol 3-kinase in cardiomyocyte dijerentiation of embryonic stem cells. FEBS Letters 476 (2000) 218-223.*
Xu et al. Endoderm and Pancreatic Islet Lineage Differentiation from Human Embryonic Stem Cells. Cloning and Stem Cells vol. 8, No. 2, 2006. p. 96-107.*
Ben Hur. T., Idelson M, Khaner H, Pera M. Reinhartz E, Itzik A, Reubinoff BE, Transplantation of human embryonic stem cell-derived neural progenitors improves behavioral deficit in Parkinsonian rats. Stem Cells. 2004;22(7):1246-55.
Calhoun. J.D., Lambert NA, Mitalipova MM, Noggle SA, Lyons I, Condie BG, Stice SL, Differentiation of rhesus embryonic stem cells to neural progenitors and neurons. Biochem Biophys Res Commun. Jun. 20, 2003;306(1):191-7.
Li, X.J., Du ZW, Zarnowska ED, Pankratz M, Hansen LO, Pearce RA, Zhang SC, Specification of motoneurons from human embryonic stem cells. Nat. Biotechnol, Feb. 2005;23(2):215-21, Epub Jan. 30, 2005.
Schulz, T.C., Noggle SA, Palmarini GM, Weiler DA, Lyons IG, Pensa, K.A., Meedeniya AC, Davidson BP, Lambert NA, Condie BG. Differentition of human embryonic stem cells to dopaminergic neurons in serum-free suspension culture. Stem Cells. 2004;22(7):1218-38.
Watanabe, K., Kamiya D, Nishiyama A, Katayama T, Nozaki S, Kawasaki H, Watanabe Y, Mizuseki K, Sasai Y, Directed differentiation of telencephalic precursors from embryonic stem cells. Nat. Neurosci. Mar. 2005;8(3):288-96. Epub Feb. 6, 2005.
Wichterle, H., Lieberam I, Porter JA, Jessell TM, Directed differentiation of embryonic stem cells into motor neurons. Cell. Aug. 9, 2002;110(3):385-97.
Ying, Q.L., Stavridis M, Griffiths D, Li M, Smith A. Conversion of embryonic stem cells into neuroectodermal precursors in adherent monoculture. Nat Biotechnol. Feb. 2003;21(2):183-6.
Zeng, X., Cai J, Chen J, Luo Y, You ZB, Fotter E, Wang Y, Harvey B, Miura T, Backman C, Chen GJ, Rao MS, Freed WJ. Dopaminergic differentiation of human embryonic stem cells. Stem Cells. 2004;22(6):925-40.
Carpenter et al., "Enrichment of Neurons and Neural Precursors From Human Embryonic Stem Cells", Experimental Neurology, Academic Press, 172, Jan. 1, 2001, 383-397.
Gottlieb, Large-Scale Sources of Neural Stem Cells, Annual Review of Neuroscience, Annual Reviews, Inc., 25, Jan. 1, 2002, 381-407.

(Continued)

*Primary Examiner* — Taeyoon Kim
(74) *Attorney, Agent, or Firm* — Woodcock Washburn, LLP

(57) ABSTRACT

This invention provides pure populations of neural precursor cells, capable of differentiation into neurons, glial cells, and astrocytes. The populations are obtained by culturing stem cell populations (such as embryonic stem cells) in a cocktail of growth conditions that initiates differentiation, and establishes the neural precursor population. The precursors can be further differentiated in culture into a variety of different neural phenotypes. The neural precursors can be generated in pure form (at least 99%) and in large quantities for use in drug screening and the treatment of neurological disorders.

18 Claims, 10 Drawing Sheets

OTHER PUBLICATIONS

Itskovitz-Eldor et al., "Differentiation of Human Embryonic Stem Cells into Embryoid Bodies Comprising the Three Embryonic Germ Layers", Molecular Medicine, Feb. 2000, 6(2), 88-95.

Reubinoff et al., "Neural Progenitors from Human Embryonic Stem Cells", Nature Biotechnology, Nature Publishing Group, Dec. 1, 2001, 19(12), 1134-1140.

Sauer et al., "Role of Reactive Oxygen Species and Phosphatidylinositol 3-Kinase in Cardiomyocyte Differentiation of Embryonic Stem Cells", FEBS Letters, Jun. 2, 2000, 476, 218-223.

Schulz et al., "Directed Neuronal Differentiation of Human Embryonic Stem Cells", BMC Neuroscience, Biomed Central, Oct. 22, 2003, 4(1), 1471-2202.

Xu et al., "Endoderm and Pancreatic Islet Lineage Differentiation from Human Embryonic Stem Cells", Cloning and Stem Cells, Jun. 6, 2006, 8(2), 96-107.

Zhang et al., In Vitro Differentiation of Transplantable Neural Precursors from Human Embryonic Stem Cells, Nature Biotechnology, Nature Publishing Group, Dec. 1, 2001, 19(12), 1129-1133.

* cited by examiner

HOMOGENEOUS NEURAL PRECURSOR CELLS

CROSS REFERENCE TO RELATED APPLICATION

This application is the National Stage of International Application No. PCT/US2006/004957, filed 9 Feb. 2006, entitled "HOMOGENEOUS NEURAL PRECURSOR CELLS", which claims the benefit of U.S. Provisional Application No. 60/651,932, filed on 9 Feb. 2005, entitled "QUANTITIVE GENERATION OF NEURAL PRECURSORS FOR HUMAN THERAPY OR DRUG SCREENING FROM EMBRYONIC CELLS," the disclosures of which are incorporated herein by reference in their entirety.

FIELD

This invention relates generally to the field of cell and developmental biology of embryonic cells. More specifically, it describes a technology for generating a substantially pure homogeneous population of neural precursor cells, and uses thereof.

BACKGROUND

Currently a major problem with the ES cell-based cell replacement therapies is cellular heterogeneity (Conley et al., *Fetal Diagn Ther* 19: 218-23, 2004). The generation of homogeneous cell populations, which are not available in sufficient quantities from fetal or adult neural tissues, is a prerequisite for clinical use. Typically, the neuronal cultures derived from mouse or human ES cells contain a variety of neuronal subtypes as well as non-neural cells. Recently, stroma-produced inductive signals and transcription factors were used to enrich for the subtypes of neurons, particularly dopaminergic neurons and motor neurons. For example, stromal co-cultures (Kawasaki et al., *Neuron* 28: 31-40, 2000) and transcription factors such as Nurr1 (Chung et al., *Eur J Neurosci* 16: 1829-38, 2002; Kim et al., *Nature* 418: 50-6, 2002) increase the generation of dopaminergic neurons. Soluble ligands, such as sonic hedgehog, increase the generation or motor neurons capable of integration into the host tissue after transplantation {Wichterle, 2002 #1933}. However, even in the best conditions, only a small percent of human ES cell-derived midbrain dopamine neurons are electrophysiologically active (Perrier et al., *Proc Natl Acad Sci USA* 101: 12543-8, 2004). The prior art cell separation techniques use magnetic beads (U.S. Pat. No. 6,833,269; Carpenter) differential digestion of rosettes (U.S. Patent Application No. 20030068819; Zhang et al.), or promoter-based isolation of neural stem cells (U.S. Patent Application No. 20040029269, Goldman et al.).

The transplantation of human Neural Precursor Cells (hNPCs) has been shown to mitigate various neurodegenerative disorders (Flax et al., *Nat. Biotechnol.* 16: 1033-1039, 1998; Tamaki et al., *J Neurosci Res* 69: 976-86, 2002; Lindvall et al., *Nat Med* 10 Suppl: S42-50, 2004). The primary human tissue is limiting and the long term in vitro expansion of hNPCs compromises their multilineage potential, migration, and differentiation capacity after transplantation (Cadwell and Joyce *PCR Methods Appl.* 2: 28-33, 1992; Schwartz et al., *J Neurosci Res* 74: 838-51, 2003). On the other hand, human Embryonic Stem (hES) cells (Thomson et al., *Science* 282: 1145-7, 1998) represent virtually unlimited source of a variety of human cell types. Several group reported that neural precursor cells (e.g., rosettes) can be found among other cells in differentiated HESC cultures can give rise to neural precursors (Carpenter et al., *Exp Neurol* 172: 383-97, 2001; Reubinoff et al., *Nat Biotechnol* 19: 1134-40, 2001; Zhang et al., *Nat Biotechnol* 19: 1129-33, 2001). All current protocols, however, use the initial formation of heterogeneous embryoid bodies and require differential enzymatic digestion (Zhang et al., *Nat Biotechnol* 19: 1129-33, 2001), extensive passaging (Reubinoff et al., *Nat Biotechnol* 19: 1134-40, 2001), and/or immuno-enrichments (Carpenter et al., *Exp Neurol* 172: 383-97, 2001). Controllable differentiation procedure resulting in homogenous target population is the key for rigorous analysis of cellular and molecular changes during hESCs to hNPCs transition and a uniform population of transplantable hNPCs is mandatory for tissue therapies in clinics (Snyder et al., *Adv. Neurol.* 72: 121-132, 1997; Odorico et al., *Stem Cells* 19: 193-204, 2001; Hornstein and Benvenisty, *J Neurosci Res* 76: 169-73, 2004).

The importance of controlled efficient differentiation of human ESC has been underscored by generation of human definitive endoderm (D'Amour et al., *Nat Biotechnol* 23: 1534-41, 2005) and generation of pure Pax-6-positive mouse neuronal precursors from mouse ES cells (Bibel et al., *Nat Neurosci* 7: 1003-9, 2004; Plachta et al., *Development* 131: 5449-56, 2004). Giving substantial differences between mouse and human ES cells (Ginis et al., *Dev Biol* 269: 360-80, 2004; Daheron et al., *Stem Cells* 22: 770-8, 2004; Humphrey et al., *Stem Cells* 22: 522-30, 2004) it is important to find out if clinically relevant human ESCs can be efficiently differentiated to homogeneous hNPCs in defined culture conditions.

Thus there is a need in the art for a method for generating large populations of highly purified, homogeneous neural precursor cells.

SUMMARY

The present invention relates to a substantially pure homogeneous population of neural precursor cells and to culture conditions and methods of culturing human neural precursor cells (hNPCs). Compositions, cell populations, cell lines and single neural precursor cells are also provided. The present invention discloses a method of obtaining a large population of a substantially pure homogeneous population of neural precursor cells. The methods of obtaining this large population of population of a substantially pure homogeneous population of neural precursor cells comprises regular culturing techniques such as cell washing and cell passaging.

In one aspect, the invention provides a method of obtaining a substantially pure homogeneous population of neural precursor cells comprising: (a) deriving the neural precursor cells from embryonic stem cells; and (b) expanding the neural precursor cells in culture media in order to produce a substantially pure homogeneous population of neural precursor cells. In some aspects, the neural precursor cells are mammalian cells. In other aspects, the mammalian neural precursor cells are human neural precursor cells (hNPCs). In some such aspects, the human neural precursor cells are multipotent. In other aspects, the embryonic stem cells are mammalian cells. In some such aspects, the embryonic stem cells are human embryonic cells. In some such aspects, the human embryonic cells are undifferentiated. In some aspects the resulting substantially pure homogeneous population of neural precursor cells is characterized by substantially reduced expression of at least one undifferentiated marker. In some such aspects, at least one undifferentiated marker is OCT4 or Nanog. In other aspects, the resulting substantially pure homogeneous population of neural precursor cells is characterized by being negative for the expression of GFAP, MAP2, GATA-1, GATA-4, Nkx2.5, PDX-1, Oct-4, Nanog, Brachyury, FoxA2, Sox17, AFP and O1. In some aspects, the resulting substantially pure homogeneous population of neural precursor cells is characterized by expression of at least one marker selected from the group consisting of Sox1, Sox2, Musashi-1, Nestin, Vimentin, and Melk. In other aspects, the resulting substantially pure homogeneous population of neural precursor cells is able to generate neurons, astrocytes, and oligodendrocytes immediately after their generation from embryonic stem cells. In some such aspects, the resulting substantially pure homogeneous population of neural precursor cells generate neurons, astrocytes, and oligodendrocytes immediately after their generation from embryonic stem cells and after at least 4 passages in vitro. In some aspects, the resulting substantially pure homogeneous population of neural precursor cells is greater than 99% neural precursor cells. In other aspects, the resulting substantially pure homogeneous population of neural precursor cells has a reproducible proteome signature over at least 55 generations.

In another aspect, the invention provides a method of differentiating primate embryonic stem cells into a substantially pure homogeneous population of neural precursor cells comprising: (a) obtaining a primate embryonic stem cell culture, (b) propagating the stem cells on feeder cells one or more days to form embryonic stem cell clusters, (c) washing the stem cell clusters at least once in a physiological medium, (d) forming the stem cell clusters into spheroid bodies in suspension medium, and (e) culturing the spheroid bodies in an expansion medium containing an effective amount of growth factor wherein a substantially pure homogeneous population of neural precursor cells is generated. In other aspects, the stem cell clusters are replated as monolayers in expansion medium. In some aspects the resulting substantially pure homogeneous population of neural precursor cells is characterized by substantially reduced expression of at least one undifferentiated marker. In some such aspects, at least one undifferentiated marker is OCT4 or Nanog. In other aspects, the resulting substantially pure homogeneous population of neural precursor cells is characterized by being negative for the expression of GFAP, MAP2, GATA-1, GATA-4, Nkx2.5, PDX-1, Oct-4, Nanog, Brachyury, FoxA2, Sox17, AFP and O1. In some aspects, the resulting substantially pure homogeneous population of neural precursor cells is characterized by expression of at least one marker selected from the group consisting of Sox1, Sox2, Musashi-1, Nestin, Vimentin, and Melk. In other aspects, the resulting substantially pure homogeneous population of neural precursor cells is able to generate neurons, astrocytes, and oligodendrocytes immediately after their generation from embryonic stem cells. In some such aspects, the resulting substantially pure homogeneous population of neural precursor cells generate neurons, astrocytes, and oligodendrocytes immediately after their generation from embryonic stem cells and after at least 4 passages in vitro. In some aspects, the resulting substantially pure homogeneous population of neural precursor cells is greater than 99% neural precursor cells. In other aspects, the resulting substantially pure homogeneous population of neural precursor cells is 100% neural precursor cells. In some aspects, the feeder cells are mEF feeder cells. In other aspects, the physiological medium is phosphate buffered saline. In some aspects, the growth factor is fibroblast growth factor (FGF) or epithelial growth factor (EGF), or a combination thereof. In some such aspects, the effective amount of FGF or EGF is at a final concentration of 20 ng/mL. In some aspects, the suspension medium or expansion medium contains an effective amount of N-acetyl cysteine (NAC). In some such aspects, the effective amount of NAC is at a final concentration of 2 mM. In other aspects, the resulting substantially pure homogeneous population of neural precursor cells has a reproducible proteome signature over at least 55 generations. In some aspects, the method further comprising culturing the spheroid bodies in expansion medium containing an effective amount of fibroblast growth factor 2 and epithelial growth factor to form adherent rosettes, dissociating the rosettes and culturing in expansion medium containing an effective amount of fibroblast growth factor 2 and epithelial growth factor to form an adherent monolayer of neural precursor cells. In some such aspects, the effective amount of fibroblast growth factor 2 and epithelial growth factor is at a final concentration of 20 ng/1 mL.

In another aspect, the invention provides a method for producing a substantially pure homogeneous neural cell population from human embryonic stem (hES) cells, comprising culturing hES cells in a medium containing one or more added growth factors, thereby producing a population in which at least 90% of the cells express Sox1, Sox2, Musashi-1, Nestin, Vimentin and Melk. In some aspects, the resulting substantially pure homogeneous neural cell population does not express GFAP, MAP2, GATA-1, GATA-4, Nkx2.5, PDX-1, Oct-4, Nanog, Brachyury, FoxA2, Sox17, AFP and O1. In other aspects, no more than 1% of the cells are negative for Sox1, Sox2, Musashi-1 and Nestin. In some aspects, no more than 10% of the cells are negative for Vimentin. In other aspects, the growth factor is fibroblast growth factor (FGF) or epithelial growth factor (EGF), or a combination thereof. In some such aspects, the effective amount of FGF or EGF is at a final concentration of 20 ng/mL. In other aspects, the medium contains an effective amount of N-acetyl cysteine (NAC). In some such aspects, the effective amount of NAC is at a final concentration of 2 mM. In other aspects, the resulting substantially pure homogeneous population of neural precursor cells has a reproducible proteome signature over at least 55 generations.

In another aspect, the invention provides a substantially pure homogeneous neural precursor cell composition generated by the methods of the invention.

In another aspect, the invention provides pharmaceutical compositions comprising the substantially pure homogeneous neural precursor cell composition and a pharmaceutically acceptable carrier.

In another aspect, the invention provides uses of the substantially pure homogeneous neural precursor cell composition for the preparation of a medicament for treatment of neuronal and related diseases. In some aspects, certain neural progenitor cells embodied in this invention are designed for treatment of acute or chronic damage to the nervous system. A variety of conditions can include epilepsy, stroke, ischemia, Huntington's disease, Parkinson's disease, amyotrophic lateral sclerosis (ALS), and Alzheimer's disease. Certain differentiated cells of this invention may also be appropriate for treating dysmyelinating disorders, such as Pelizaeus-Merzbacher disease, multiple sclerosis, leukodystrophies, neuritis and neuropathies.

In another aspect, the invention provides uses of the substantially pure homogeneous neural precursor cell composition in human cell therapy and gene therapy. In some aspects, certain neural progenitor cells embodied in this invention are designed for treatment of acute or chronic damage to the nervous system. A variety of conditions can include epilepsy, stroke, ischemia, Huntington's disease, Parkinson's disease, amyotrophic lateral sclerosis (ALS), and Alzheimer's disease. Certain differentiated cells of this invention may also be appropriate for treating dysmyelinating disorders, such as Pelizaeus-Merzbacher disease, multiple sclerosis, leukodystrophies, neuritis and neuropathies.

DETAILED DESCRIPTION

Introduction and Overview

Figure 1:
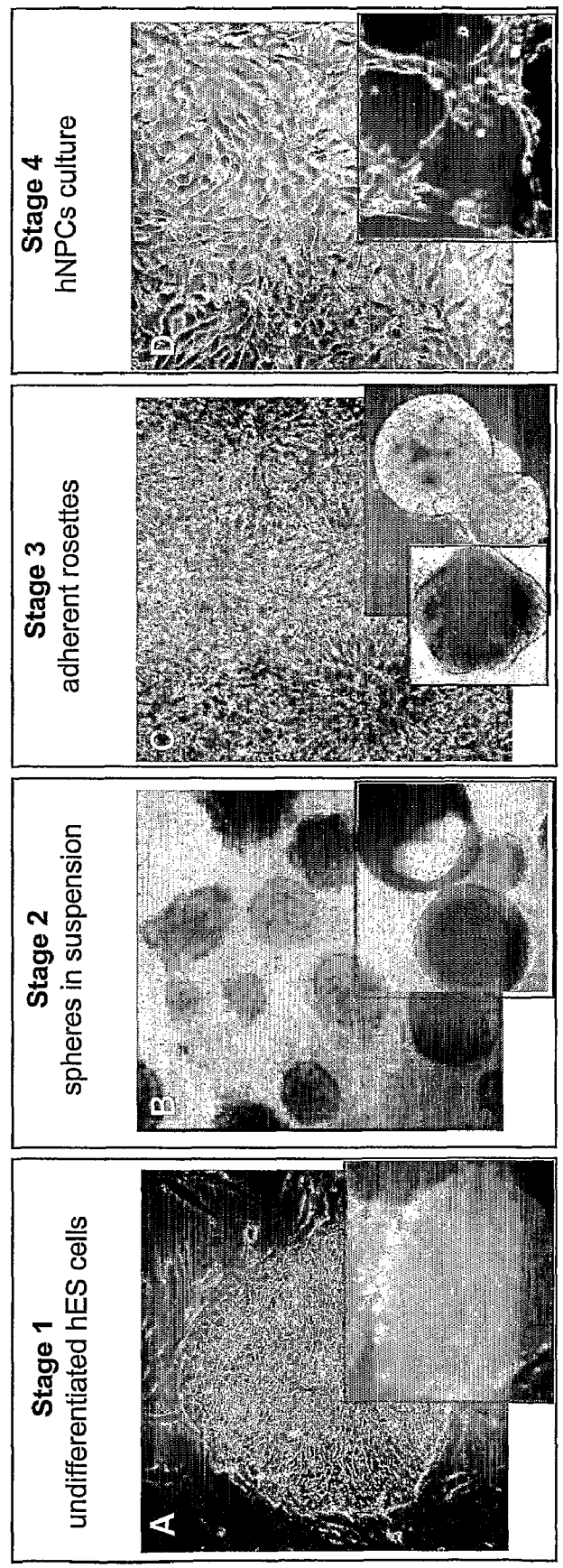
FIG. 1. Schematic representation of hNPC derivation process. A, Stage 1, the colonies of entirely undifferentiated human ES cells as illustrated by the hESC-H9 line expressing GFP under the Oct4 promoter confirming the uniformly undifferentiated state of hESCs (insert in A). B, Stage 2, the compact spheres appear 4-6 days after dissociation using collagenaseIV and repeated washes with PBS; care was taken to avoid large clumps that invariably resulted in spheroid bodies with cavities and layers (insert in B). C, Stage 3, the spheres transferred to the expansion medium form attached rosettes and cells radiating out of the clusters; some still floating spheres were composed entirely of rosettes (insert in C). D, Stage 4, four days later (~8-10 days from the beginning of differentiation protocol) stage 3 cells were collected with Ca/Mg free PBS, triturated to single cells and replated in expansion medium on ornithine coated dishes. The attached cells initially appeared as a monolayer of triangular/bipolar cells, which later tend to grow in clusters and form lattices (inset in D).

Human Embryonic stem (hES) cells provide a virtually unlimited source of clonal/genetically modified cells potentially useful for tissue replacement therapies. A reliable method for generating a homogeneous population of transplantable neural precursors is a prerequisite both for clinical application and our understanding of the mechanisms that drive developmental decisions.

Stem cell-based therapies for neurodegeneration and CNS trauma will require large quan-tities of well-characterized homogeneous human neural precursors. Human embryonic stem cells (hESCs) are ideally positioned as an unlimited source of such cells, providing a simple and efficient protocol for generation of hESC-derived neural precursors (hES-NPCs) is available. As disclosed herein, we have developed a controlled procedure of rapid (~12 days) and efficient (over 99%) conversion of hESCs into hNPCs using defined medium. Whole-cell proteome profiling provided evidence of reproducible conversion of hESCs that have been expanded over $10^{15}$ folds. Because of the high purity of the end cultures of hES-NPCs we were able for the first time to investigate the pattern of gene expression during transition from human ES cells to neural precursors. The cells generated in by the disclosed methods are capable of efficient in vitro differentiation into neurons, which have electrophisological properties expected for young human neurons and abundant oligodendrocytres capable of in vitro myelination of the neuronal processes in the same culture. Furthermore, the hES-NPCs can migrate and differentiate upon transplantation into neonate mice and rescuing the myelination pathology in corpus callosum upon the injection into the Cuprizone-induced demyelination model. The hES-NPCs derivation procedure presented in our work will be helpful for obtaining relevant populations of human neural precursors for transplantation in clinics and for use in high-throughput screening of drugs.

A procedure for efficient differentiation of HESC to neural precursor cells (hES-NPCs) homogenous with respect to the markers used is described. Large quantities of hES-NPCs, uniformly positive for early neural precursor markers Sox1, Sox2, Nestin, and Musashi1, have been generated by the methods disclosed.

As described herein, hES cells (H9 and H14 NIH approved lines) are used to derive a homogeneous population of transplantable cells expressing the markers of adult Neural Precursor Cells (hNPCs). The invention provides a well-controlled procedure for the differentiation of hES cells into a population of neural precursors morphologically indistinguishable from adult human brain derived NPCs and uniformly positive for Sox1, Sox2, Nestin and Musashi markers. These hES derived NPCs are able to generate neurons, astrocytes and oligodendrocytes immediately after their generation from hES cells as well as after at least 4 passages in vitro.

The invention provides a number of methods, reagents, and compounds. It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a cell" includes a combination of two or more cells, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

Stem cells are undifferentiated cells defined by their ability at the single cell level to both self-renew and differentiate to produce progeny cells, including self-renewing progenitors, non-renewing progenitors and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent—able to give rise to all embryonic and extraembryonic cell types; (2) pluripotent—able to give rise to all embryonic cell types; (3) multipotent—able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood); (4) oligopotent—able to give rise to a more restricted subset of cell lineages than multipotent stem cells; and (5) unipotent—able to give rise to a single cell lineage (e.g., spermatogenic stem cells).

Differentiation is the process by which an unspecialized ("uncommitted") or less specialized cell acquires the features of a specialized cell, such as a nerve cell or a muscle cell, for example. A differentiated or differentiation-induced cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

In a broad sense, a progenitor cell is a cell that has the capacity to create progeny that are more differentiated than itself and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

For the purposes of this disclosure, "neural progenitor cell" or "neural precursor cell" mean a cell that can generate progeny that are either neuronal cells (such as neuronal precursors or mature neurons) or glial cells (such as glial precursors, mature astrocytes, or mature oligodendrocytes). Typically, the cells express some of the phenotypic markers that are characteristic of the neural lineage as described below. Typically, they do not produce progeny of other embryonic germ layers when cultured by themselves in vitro, unless dedifferentiated or reprogrammed in some fashion. Neural precursor cells give rise to all types of neural cells: neurons, astrocytes and oligodendrocytes. Neural precursor cells, as used herein, describes a cell that is capable of undergoing greater than 20-30 cell divisions while maintaining the potency to generate neurons, astrocytes and oligodendrocytes. Preferably, said cells are capable of undergoing greater than 40, more preferably greater than 50, most preferably unlimited such cell divisions.

A "multipotent neural progenitor cell population" is a cell population that has the capability to generate both progeny that are neuronal cells (such as neuronal precursors or mature neurons), and progeny that are glial cells (such as glial precursors, mature astrocytes, or mature oligodendrocytes), and sometimes other types of cells. The term does not require that individual cells within the population have the capability of forming both types of progeny, although individual cells that are multipotent neural progenitors may be present.

A "differentiation agent", as used in this disclosure, refers to one of a collection of compounds that are used in culture systems of this invention to produce differentiated cells of the neural lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others, or acting in concert with other agents through unknown mechanisms.

Reference herein to a "population" of cells means two or more cells. A "homogeneous population" means a population comprising substantially only one cell type. A "cell type" may be cells of the same lineage or sub-type having substantially the same physiological status. Preferred homogeneous populations of the invention comprise substantially only early neuro-ectoderm-like Neural Precursor Cells (hNPCs). Reference to a "substantially pure homogeneous population of nNPCs" refers to a human neural progenitor cell population in which a substantial number of the total population of the cells are of the same type and/or are in the same state of differentiation. Preferably, a "substantially pure homogeneous population" of neural cell precursor cells comprises a population of cells of which at least about 50% are of the same cell type, more preferably that at least about 75% are of the same cell type, even more preferably at least about 85% are of the same cell type, still even more preferably at least about 95% of the cells are the same type, and even more preferably at least about 97%, 98%, 99% or 100% are of the same cell type. In one embodiment, the preferred substantially homogeneous population of the invention is at least 99% of the same cell type. In another preferred embodiment, the preferred substantially homogeneous population of the invention is 100% of the same cell type. The substantially pure homogeneous population of hNPCs are generally obtained after about 10-12 days following the methods as disclosed herein.

Unless explicitly indicated otherwise, the techniques of this invention can be brought to bear without restriction on any type of progenitor cell capable of differentiating into neuronal or glial cells.

Prototype "primate Pluripotent Stem cells" (pPS cells) are pluripotent cells derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice.

Included in the definition of pluripotent stem cells are embryonic cells of various types, exemplified by human embryonic stem (hES) cells, described by Thomson et al., *Science* 282: 1145, 1998; embryonic stem cells from other primates, such as Rhesus stem cells (Thomson et al., *Proc. Natl. Acad. Sci. USA* 92: 7844, 1995), marmoset stem cells (Thomson et al., *Biol. Reprod.* 55: 254, 1996) and human embryonic germ (hEG) cells (Shamblott et al., *Proc. Natl. Acad. Sci. USA* 95: 13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. The pPS cells are not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells within the population will often be surrounded by neighboring cells that are differentiated.

"Feeder cells" or "feeders" are terms used to describe cells of one type that are co-cultured with cells of another type, to provide an environment in which the cells of the second type can grow. For example, certain types of pPS cells can be supported by primary mouse embryonic fibroblasts, immortalized mouse embryonic fibroblasts, or human fibroblast-like cells differentiated from hES cell. pPS cell populations are said to be "essentially free" of feeder cells if the cells have been grown through at least one round after splitting in which fresh feeder cells are not added to support the growth of the pPS.

"Embryoid bodies" is a term of art synonymous with "aggregate bodies". The terms refer to aggregates of differentiated and undifferentiated cells that appear when pPS cells overgrow in monolayer cultures, or are maintained in suspension cultures. Embryoid bodies are a mixture of different cell types, typically from several germ layers, distinguishable by morphological criteria and cell markers detectable by immunocytochemistry.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

Various terms are used to describe cells in culture. Cell culture refers generally to cells taken from a living organism and grown under controlled condition ("in culture"). A primary cell culture is a culture of cells, tissues or organs taken directly from organisms and before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, and time between passaging.

As will be appreciated by those skilled in the art, "culturing the hES cells" or "culturing the hNPCs", means culturing the cells under conditions which allow for the survival of the cells for a length of time sufficient to allow for experimentation and further use of the cells. The culturing of the cells the understanding that the conditions under which the cells are cultured are appropriate for the continued survival of the cells for the purposes for which the cells are being used.

The terms "protein expression profile", "protein expression signature", "protein expression fingerprint" and "proteome signature" as used herein refer to the expression pattern of proteins representing a particular cell or tissue type (e.g., human neural progenitor cells) as analyzed as disclosed herein (see Examples). The proteome signature, for example, can be monitored after passaging cells over several generations.

"Modulate" as used herein is meant, in one context, the ability of a compound to alter the protein expression fingerprint or proteome signature of a cell or tissue. Preferably, a drug candidate will be identified by its ability to alter the fingerprint or signature of a cell towards the profile of the corresponding normal, non-disease cell.

"Change" includes "increase" and "decrease" and refers to the relative increase or decrease in abundance of a proteome signature or the relative increase or decrease in expression or activity of a proteome signature in a first sample or sample set compared to a second sample (or sample set). A change may be measured by any technique known to those of skill in the art, albeit the observed increase or decrease will vary depending upon the technique used. Preferably, change is determined herein as described in the Examples infra.

As used herein, standard growth conditions refers to standard atmospheric conditions comprising about 5% $CO_2$, a temperature of about 30-40° C., preferably between about 32-38° C., most preferably between about 35-37° C., and a relative humidity of about 100%.

"Isolated" refers to a cell, cellular component, or a molecule that has been removed from its native environment.

"Modulator" includes inhibitors and activators. Inhibitors are agents that, e.g., bind to, partially or totally block stimulation, decrease, prevent, delay activation, inactivate, desensitize, or down regulate the activity of a polypeptide or polynucleotide of the invention, e.g., antagonists. Activators are agents that, e.g., bind to, stimulate, increase, open, activate, facilitate, enhance activation, sensitize or up regulate the activity of a polypeptide or polynucleotide of the invention, e.g., agonists. Modulators include agents that, e.g., alter the interaction of the chemokines of the invention with: proteins that bind activators or inhibitors, receptors, including proteins, peptides, lipids, carbohydrates, polysaccharides, or combinations of the above, e.g., lipoproteins, glycoproteins, and the like. Modulators include genetically modified versions of naturally-occurring ligands, e.g., with altered activity, as well as naturally occurring and synthetic ligands, antagonists, agonists, small chemical molecules and the like. "Cell-based assays" for inhibitors and activators include, e.g., applying putative modulator compounds, e.g., small molecules, drugs, chemokines and the like, to a cell expressing a particular gene or genes of interest and then determining the functional effects on the particular genes related to cell proliferation and viral replication, as described herein. "Cell based assays" include, but are not limited to, in vivo tissue or cell samples from a mammalian subject or in vitro cell-based assays comprising a particular gene or genes of interest that are treated with a potential activator, inhibitor, or modulator are compared to control samples without the inhibitor, activator, or modulator to examine the extent of inhibition. Control samples (untreated with inhibitors) can be assigned a relative activity value of 100%. Inhibition of cell proliferation, for example, is achieved when the activity value relative to the control is about 80%, optionally 50% or 25-0%. Activation of a particular activity is achieved when the activity value relative to the control is 110%, optionally 150%, optionally 200-500%, or 1000-3000% higher.

"Treating" or "treatment" refers to any indication of success in amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" includes the administration of the construct or agents of the present invention to prevent or delay, to alleviate, or to arrest or inhibit development of the symptoms or conditions associated with the disease, condition or disorder. "Therapeutic effect" refers to the reduction, elimination, or prevention of the disease, symptoms of the disease, or side effects of a disease, condition or disorder in the subject. Treatment may be prophylactic (to prevent or delay the onset of the disease, condition or disorder, or to prevent the manifestation of clinical or subclinical symptoms thereof) or therapeutic suppression or alleviation of symptoms after the manifestation of the disease, condition or disorder.

In general, the phrase "well tolerated" refers to the absence of adverse changes in health status that occur as a result of the treatment and would affect treatment decisions.

"In combination with", "combination therapy" and "combination products" refer, in certain embodiments, to the concurrent administration to a patient of a first therapeutic and the compounds and cells as cells as described herein. When administered in combination, each component can be administered at the same time or sequentially in any order at different points in time. Thus, each component can be administered separately but sufficiently closely in time so as to provide the desired therapeutic effect "Subject", "mammalian subject" or "patient" refers to any mammalian patient or subject to which the compositions of the invention can be administered. "Mammal" or "mammalian" refers to human patients and non-human primates, as well as experimental animals such as rabbits, rats, and mice, and other animals. In an exemplary embodiment, of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that can be associated with the targeted or suspected disease or condition. These and other routine methods allow the clinician to select patients in need of therapy using the methods and formulations of the invention.

"Pharmaceutically acceptable carrier (or medium)", which may be used interchangeably with "biologically compatible carrier or medium", refers to reagents, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds). As used herein, the term biodegradable describes the ability of a material to be broken down (e.g., degraded, eroded, dissolved) in vivo. The term includes degradation in vivo with or without elimination (e.g., by resorption) from the body. The semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

Several terms are used herein with respect to cell replacement therapy. The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

"Transformed cell" means a cell into which (or into predecessor or an ancestor of which) a nucleic acid molecule encoding a polypeptide of the invention has been introduced, by means of, for example, recombinant DNA techniques or viruses.

"Nucleic acid" or "nucleic acid molecule" refer to a deoxyribonucleotide or ribonucleotide polymer in either single- or double-stranded form, and unless otherwise limited, can encompass known analogs of natural nucleotides that can function in a similar manner as naturally occurring nucleotides. A "control element" or "control sequence" is a nucleotide sequence involved in an interaction of molecules that contributes to the functional regulation of a polynucleotide, such as replication, duplication, transcription, splicing, translation, or degradation of the polynucleotide. Transcriptional control elements include promoters, enhancers, and repressors.

Particular gene sequences referred to as promoters, are polynucleotide sequences derived from the gene referred to that promote transcription of an operatively linked gene expression product. It is recognized that various portions of the upstream and intron untranslated gene sequence may in some instances contribute to promoter activity, and that all or any subset of these portions may be present in the genetically engineered construct referred to. The promoter may be based on the gene sequence of any species having the gene, unless explicitly restricted, and may incorporate any additions, substitutions or deletions desirable, as long as the ability to promote transcription in the target tissue. Genetic constructs designed for treatment of humans typically comprise a segment that is at least 90% identical to a promoter sequence of a human gene. A particular sequence can be tested for activity and specificity, for example, by operatively linking to a reporter gene.

Genetic elements are said to be "operatively linked" if they are in a structural relationship permitting them to operate in a manner according to their expected function. For instance, if a promoter helps initiate transcription of the coding sequence, the coding sequence can be referred to as operatively linked to (or under control of) the promoter. There may be intervening sequence between the promoter and coding region so long as this functional relationship is maintained.

In the context of encoding sequences, promoters, and other genetic elements, the term "heterologous" indicates that the element is derived from a genotypically distinct entity from that of the rest of the entity to which it is being compared. For example, a promoter or gene introduced by genetic engineering techniques into an animal of a different species is said to be a heterologous polynucleotide. An "endogenous" genetic element is an element that is in the same place in the chromosome where it occurs in nature, although other elements may be artificially introduced into a neighboring position.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but which functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxy-biphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

"Polypeptide" includes proteins, fusion proteins, oligopeptides and polypeptide derivatives, with the exception that peptidomimetics are considered to be small molecules herein.

A "protein" is a molecule having a sequence of amino acids that are linked to each other in a linear molecule by peptide bonds. Protein refers to a polypeptide that is isolated from a natural source, or produced from an isolated cDNA using recombinant DNA technology; and has a sequence of amino acids having a length of at least about 200 amino acids.

A "fusion protein" is a type of recombinant protein that has an amino acid sequence that results from the linkage of the amino acid sequences of two or more normally separate polypeptides.

A "protein fragment" is a proteolytic fragment of a larger polypeptide, which may be a protein or a fusion protein. A proteolytic fragment may be prepared by in vivo or in vitro proteolytic cleavage of a larger polypeptide, and is generally too large to be prepared by chemical synthesis. Proteolytic fragments have amino acid sequences having a length from about 200 to about 1,000 amino acids.

An "oligopeptide" or "peptide" is a polypeptide having a short amino acid sequence (i.e., 2 to about 200 amino acids). An oligopeptide is generally prepared by chemical synthesis.

"Antibody" as used in this disclosure refers to both polyclonal and monoclonal antibody. The ambit of the term deliberately encompasses not only intact immunoglobulin molecules, but also such fragments and derivatives of immunoglobulin molecules (such as single chain Fv constructs, diabodies, and fusion constructs) as may be prepared by techniques known in the art, and retaining a desired antibody binding specificity.

For further elaboration of general techniques useful in the practice of this invention, the practitioner can refer to standard textbooks and reviews in cell biology, tissue culture, and embryology. Included are Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in vitro (Wiles, *Meth. Enzymol.* 225: 900, 1993); Properties and uses of Embryonic Stem Cells: Prospects for Application to Human Biology and Gene Therapy (Rathjen et al., *Reprod. Fertil. Dev.* 10: 31, 1998).

For elaboration of nervous system abnormalities, and the characterization of various types of nerve cells, markers, and related soluble factors, the reader is referred to CNS Regeneration: Basic Science and Clinical Advances, M. H. Tuszynski & J. H. Kordower, eds., Academic Press, 1999.

In accordance with the present invention, there can be employed conventional molecular biology, microbiology, immunology, and recombinant DNA techniques within the skill of the art. Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature. Methods in molecular genetics and genetic engineering are described the series Methods in Enzymology (Academic Press); Gene Transfer Vectors for Mammalian Cells (J. M. Miller & M. P. Calos, eds., 1987); Recombinant DNA Methodology II (R. Wu ed., Academic Press 1995); Sambrook, Fitsch & Maniatis, 1989, Molecular Cloning: A Laboratory Manual, $2^{nd}$, Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (Hames, B. D. & S. J. Higgins, eds. 1984); Animal Cell Culture (R. I. Freshney, ed. 1986); Immobilized Cells and Enzymes (IRL Press, 1986); B. E. Perbal, 1984, A Practical Guide to Molecular Cloning; F. M. Ausubel et al. (eds.), Current Protocols in Molecular Biology, 1997, John Wiley & Sons, Inc., N. C. Dracopoli et al. (eds.), Current Protocols in Human Genetics, 1997, John Wiley & Sons, Inc., A. D. Baxevanis et al. (eds.), Current Protocols in Bioinformatics, 1992, John Wiley & Sons, Inc.; Laboratory Techniques In Biochemistry And Molecular Biology: Hybridization With Nucleic Acid Probes, Part I. Theory and Nucleic Acid Preparation, Tijssen, ed. Elsevier, N.Y., 1993 (these references are herein incorporated by reference in their entirety for all purposes). Reagents, cloning vectors, and kits for genetic manipulation referred to in this disclosure are available from commercial vendors such as BioRad, Stratagene, Invitrogen, and ClonTech.

General techniques used in raising, purifying and modifying antibodies, and the design and execution of immunoassays including immunohistochemistry, the reader is referred to Handbook of Experimental Immunology (D. M. Weir & C. C. Blackwell, eds.); Current Protocols in Immunology (J. E. Coligan et al., eds., 1991); and R. Masseyeff, W. H. Albert, and N. A. Staines, eds., Methods of Immunological Analysis (Weinheim: VCH Verlags GmbH, 1993).

Stem Cells

This invention can be practiced using stem cells of various types, which can include the following non-limiting examples.

Multipotent neural stem cells obtained from brain tissue (see, e.g., U.S. Pat. No. 5,851,832. Neuroblasts can be produced from newborn cerebral hemispheres (see, e.g., U.S. Pat. No. 5,766,948. Mammalian neural crest stem cells can also be isolated (see, e.g., U.S. Pat. Nos. 5,654,183 and 5,849,553). U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain and cultured with a medium comprising glucose, transferrin, insulin, selenium, progesterone, and several other growth factors.

Primary liver cell cultures can be obtained from human biopsy or surgically excised tissue by perfusion with an appropriate combination of collagenase and hyaluronidase. Alternatively, EP 0 953 633 A1 reports isolating liver cells by preparing minced human liver tissue, resuspending concentrated tissue cells in a growth medium and expanding the cells in culture. The growth medium comprises glucose, insulin, transferrin, $T_3$, FCS, and various tissue extracts that allow the hepatocytes to grow without malignant transformation. The cells in the liver are thought to contain specialized cells including liver parenchymal cells, Kupffer cells, sinusoidal endothelium, and bile duct epithelium, and also precursor cells (referred to as "hepatoblasts" or "oval cells") that have the capacity to differentiate into both mature hepatocytes or biliary epithelial cells (Rogler, *Am. J. Pathol.* 150: 591, 1997; Alison, *Current Opin. Cell Biol.* 10: 710, 1998; Lazaro et al., *Cancer Res.* 58: 514, 1998).

Methods for isolating human neonatal or fetal hematopoietic stem or progenitor cells have also been reported (see, e.g., U.S. Pat. No. 5,192,553). U.S. Pat. No. 5,716,827 reports human hematopoietic cells that are Thy-1 positive progenitors, and appropriate growth media to regenerate them in vitro. A method and device for culturing human hematopoietic cells and their precursors has been reported in U.S. Pat. No. 5,635,387. U.S. Pat. No. 6,015,554 describes a method of reconstituting human lymphoid and dendritic cells.

U.S. Pat. No. 5,486,359 reports homogeneous populations of human mesenchymal stem cells that can differentiate into cells of more than one connective tissue type, such as bone, cartilage, tendon, ligament, and dermis. They are obtained from bone marrow or periosteum. Also reported are culture conditions used to expand mesenchymal stem cells. WO 99/01145 reports human mesenchymal stem cells isolated from peripheral blood of individuals treated with growth factors such as G-CSF or GM-CSF. WO 00/53795 reports adipose-derived stem cells and lattices, substantially free of adipocytes and red cells. These cells reportedly can be expanded and cultured to produce hormones and conditioned culture media.

The invention can be practiced using stem cells of any vertebrate species. Included are stem cells from humans; as well as non-human primates, domestic animals, livestock, and other non-human mammals.

Amongst the stem cells suitable for use in this invention are primate pluripotent stem (pPS) cells derived from tissue formed after gestation, such as a blastocyst, or fetal or embryonic tissue taken any time during gestation.

Non-limiting examples are primary cultures or established lines of embryonic stem cells. In a preferred embodiment, the adult neural precursor cells (hNPCs) of the invention are derived from H9 and H14 NIH hES approved lines.

Media and Feeder Cells

Media for isolating and propagating hNPCs can have any of several different formulas, as long as the cells obtained have the desired characteristics, and can be propagated further.

Although stem cells may be derived from any tissue harboring stem cells, in particular embodiments they are from bone marrow, embryos, mesenchyme, neural tissue, pancreatic tissue, muscle tissue (such as cardiac muscle), liver, skin, intestine, nasal epithelium, bone, pancreas, or germ cells, for example. A skilled artisan recognizes that the culture media may be supplemented with growth factors to facilitate culturing or expansion, appropriate to the cells/tissue from which the stem cells originally derive or appropriate to the cells/tissue to which the stem cells will differentiate. For example, for embryonic stem cells, expansion factors ex vivo may include one or more of the following: FGFβ, Wnt-3a, collagen, fibronectin, and laminin. For mesenchymal stem cells, for example, expansion factors ex vivo may include one or more FGFβ, EGF, PDGF, and fibronectin. For haematopoietic stem cells, expansion factors ex vivo may include one or more of IL-3, IL-6, stem cell factor (SCF), β-mercaptoethanol, Flt-3/Flk-2, Tpo, Shh, Wnt-3a, and Kirre. For neural stem cells, ex vivo expansion factors may include one or more of FGFβ, EGF, fibronectin, and cystatin C. For liver stem cells, expansion factors ex vivo may include one or more of leukemia inhibitory factor, LIF, IL-3, SCF, and Flt-3 ligand. For cardiac muscle stem cells, expansion factors ex vivo may include fibronectin. For intestinal stem cells, expansion factors ex vivo may include macrophage colony-stimulating factor and granulocyte-macrophage colong-stimulating factor. For pancreatic stem cells, expansion factors ex vivo may include FGF. A skilled artisan recognizes that analogous suitable reagents may be applied for any particular type of stem cells.

In some embodiments, the media can include at least some media transferred from a previous culture media, which may be considered to be "conditioned," wherein cells have previously secreted useful agents such as growth factors and cytokines into the media. Any agents that facilitate growth of the stem cells in the media and/or any agents that enhance the ability to distinguish the suspended cells from the adherent cells are useful in the invention. Specific examples of conditioning agents may be dependent upon the tissue from which the original plurality of cells were derived for the isolation of the stem cells. Exemplary growth factors and cytokines include leukotrienes; second messengers (e.g., cAMP, cGMP); growth factor EGF, FGF, PDGF, BMP, GDNF; or interleukins provided by the medium (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29); and vitamins. In alternative embodiments, these growth factors and cytokines are not obtained from the conditioned media but are added exogenously, although they may also be used to supplement conditioned media having the same or different agents.

In a preferred embodiment, hESCs are initially grown in Suspension Medium (1:1 ratio of DMEM/F12:neurobasal medium with N2+B27 supplements, 20 ng/ml insulin 20 ng/ml bFGF, 20 ng/ml EGF and 2 mM N-acetyl cysteine (NAC)). The spheres are grown for 4-6 days, with a change in medium every alternate day. Spheres are collected, gently triturated and plated on ornithin coated (5 ng/ml, Sigma) plates (Corning) in the hNPCs.

In another preferred embodiment, the stem cells are then grown in Expansion Medium (DMEM/F12, 10% BIT 9500, 20 ng/ml bFGF, 20 ng/ml EGF, 5 μg/ml fibronectin, 2 μg/ml heparin) for another 4 days to obtain the monolayers of hES-NPCs.

In another preferred embodiment, the hESCs can be grown directly in Expansion Medium bypassing the initial growth period in Suspension Medium. However, for cells bypassing the growth period in Suspension Medium, 2 mMM NAC is added to the Expansion Medium prior to use.

Feeder cells (where used) are propagated in mEF medium, containing 90% DMEM; 10% FBS, and 2 mM glutamine. mEFs are propagated in T150 flasks, splitting the cells 1:2 every other day with trypsin, keeping the cells subconfluent. To prepare the feeder cell layer, cells are irradiated at a dose to inhibit proliferation but permit synthesis of important factors that support hES cells (approximately 4000 rads gamma irradiation). Six-well culture plates are coated by incubation at 37° C. with 1 mL 0.5% gelatin per well overnight, and plated with 375,000 irradiated mEFs per well. Feeder cell layers are typically used 5 h to 4 days after plating. The medium is replaced with fresh hES medium just before seeding hES cells.

Conditions for culturing other stem cells are known, and can be optimized appropriately according to the cell type. Media and culture techniques for particular cell types referred to in the previous section are provided in the references cited.

Differentiated Cell Phenotypes

In the two dimensions of a standard microscopic image, hESCs have high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland, Calif.) and compared to published human karyotypes.

hESCs and hNPCs can also be characterized by expressed cell markers. In general, the tissue-specific markers discussed herein can be detected using a suitable immunological technique, such as flow cytometry for membrane-bound markers, immunohistochemistry for intracellular markers, and enzyme-linked immunoassay, for markers secreted into the medium. The expression of protein markers can also be detected at the mRNA level by reverse transcriptase-PCR using marker-specific primers. See, e.g., U.S. Pat. No. 5,843,780.

Cells can be characterized according to a number of phenotypic criteria. The criteria include but are not limited to characterization of morphological features, detection or quantitation of expressed cell markers and enzymatic activity, and determination of the functional properties of the cells in vivo.

Markers of interest for neural cells include β-tubulin III or neurofilament, characteristic of neurons; glial fibrillary acidic protein (GFAP), present in astrocytes; galactocerebroside (GalC) or myelin basic protein (MBP); characteristic of oligodendrocytes; OCT-4, characteristic of undifferentiated hES cells; nestin, characteristic of neural precursors and other cells. A2B5 and NCAM are characteristic of glial progenitors and neural progenitors, respectively. Cells can also be tested for secretion of characteristic biologically active substances. For example, GABA-secreting neurons can be identified by production of glutamic acid decarboxylase or GABA. Dopaminergic neurons can be identified by production of dopa decarboxylase, dopamine, or tyrosine hydroxylase.

The substantially pure homogeneous population of hNPCs of the present invention express at least one (and preferably all) of the following markers: Sox1, Sox2, Musashi 1, Nestin, Vimentin, and Melk. The substantially pure homogeneous population of hNPCs of the present invention are negative for the expression of at least one (preferably both) of Oct-4 and Nanog. The substantially pure homogeneous population of hNPCs of the invention are also negative for the expression of GFAP, MAP2, GATA-1, GATA-4, Nkx2.5, PDX-1, Oct-4, Nanog, Brachyury, FoxA2, Sox17, AFP and O1. See also the Examples and FIG. 4.

In another embodiment, the substantially pure homogeneous population of hNPCs of the invention are uniformly negative (99% or more negative) for GFAP, MAP2, GATA-1, GATA-4, Nkx2.5, PDX-1, Oct-4, Nanog, Brachyury, FoxA2, Sox17, AFP and O1; uniformly positive (99% or more positive) for Sox1, Sox2, Musashi 1, Nestin and Melk. In another preferred embodiment, the substantially pure homogeneous population of hNPCs of the invention are also 90% or more positive for vimentin.

Freshly generated hES-NPCs are negative for the GFAP marker; however, upon passaging, the cells emigrating from the clusters and then all cells in the cultures acquired the GFAP marker. In some embodiments, Brachyury/T, Sox17 and alpha-fetoprotein (AFP) are detected in the hES-NPCs after four to six days in Suspension Medium; however these markers are not detected in the hES-NPCs after four days of further propagation in the hNPCs Expansion Medium.

In another embodiment, the present invention is a substantially pure homogeneous cell population comprising at least 90%, preferably 95%, and more preferably 99%, and most preferably 100% substantially pure homogeneous population of hNPCs. The substantially pure homogeneous population of hNPCs can be defined by being positive for Sox1, Sox2, Musashi 1 and Nestin. In another embodiment, the substantially pure homogeneous population of hNPCs can be defined by being positive for Sox1, Sox2, Musashi 1, Nestin and vimentin. In another embodiment, the substantially pure homogeneous population of hNPCs can be defined by being positive for Sox1, Sox2, Musashi 1, Nestin, vimentin, and Melk.

Certain tissue-specific markers listed herein or known in the art can be detected by immunological techniques, such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (www.ncbi.nlm.nih.gov:80/entrez).

Recombinant Nucleic Acid Techniques

The nucleic acids used to practice this invention, whether RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

To measure the transcription level (and thereby the expression level) of a gene or genes, a nucleic acid sample comprising mRNA transcript(s) of the gene or genes, or nucleic acids derived from the mRNA transcript(s) is provided. A nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample. Thus, suitable samples include mRNA transcripts of the gene or genes, cDNA reverse transcribed from the mRNA, cRNA transcribed from the cDNA, DNA amplified from the genes, RNA transcribed from amplified DNA, and the like.

In some methods, a nucleic acid sample is the total mRNA isolated from a biological sample. The term "biological sample", as used herein, refers to a sample obtained from an organism or from components (e.g., cells) or an organism. The sample can be of any biological tissue or fluid. Frequently the sample is from a patient. Such samples include sputum, blood, blood-cells (e.g., white cells), tissue or fine needle biopsy samples, urine, peritoneal fluid, and fleural fluid, or cells therefrom. Biological samples can also include sections of tissues such as frozen sections taken for histological purposes. Often two samples are provided for purposes of comparison. The samples can be, for example, from different cell or tissue types, from different species, from different individuals in the same species or from the same original sample subjected to two different treatments (e.g., drug-treated and control).

The invention includes polynucleotides encoding chemokines of the invention. As used herein, "polynucleotide" refers to a polymer of deoxyribonucleotides or ribonucleotides, in the form of a separate fragment or as a component of a larger construct. DNA encoding a chemokine of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code. Such polynucleotides are useful for the recombinant production of large quantities of a peptide of interest.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

Alternatively, these nucleic acids can be synthesized in vitro by well-known chemical synthesis techniques, as described in, e.g., Adams, *J. Am. Chem. Soc.* 105: 661, 1983; Belousov, *Nucleic Acids Res.* 25: 3440-3444, 1997; Frenkel, *Free Radic. Biol. Med.* 19: 373-380, 1995; Blommers, *Biochemistry* 33: 7886-7896, 1994; Narang, *Meth. Enzymol.* 68: 90, 1979; Brown, *Meth. Enzymol.* 68: 109, 1979; Beaucage, *Tetra. Let.* 22: 1859, 1981; U.S. Pat. No. 4,458,066.

The invention provides oligonucleotides comprising sequences of the invention, e.g., subsequences of the exemplary sequences of the invention. Oligonucleotides can include, e.g., single stranded poly-deoxynucleotides or two complementary polydeoxynucleotide strands which can be chemically synthesized.

In accordance with the present invention, there can be employed conventional molecular biology, microbiology, immunology, and recombinant DNA techniques within the skill of the art. Such techniques are explained fully in the literature. Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., See, for example, Sambrook, Fitsch & Maniatis, 1989, Molecular Cloning: A Laboratory Manual, $2^{nd}$, Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (Hames, B. D. & S. J. Higgins, eds. 1984); Animal Cell Culture (R. I. Freshney, ed. 1986); Immobilized Cells and Enzymes (IRL Press, 1986); B. E. Perbal, 1984, A Practical Guide to Molecular Cloning; F. M. Ausubel et al. (eds.), Current Protocols in Molecular Biology, 1997, John Wiley & Sons, Inc., N. C. Dracopoli et al. (eds.), Current Protocols in Human Genetics, 1997, John Wiley & Sons, Inc., A. D. Baxevanis et al. (eds.), Current Protocols in Bioinformatics, 1992, John Wiley & Sons, Inc.; Laboratory Techniques In Biochemistry And Molecular Biology: Hybridization With Nucleic Acid Probes, Part I. Theory and Nucleic Acid Preparation, Tijssen, ed. Elsevier, N.Y., 1993 (these references are herein incorporated by reference in their entirety for all purposes).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, adioimmunoassay (RIAs), enzyme-linked immunosorbent assays (ELISAs), immunofluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be done by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld, *Nat. Genet.* 15: 333-335, 1997; yeast artificial chromosomes (YAC); bacterial artificial chromosomes (BAC); P1 artificial chromosomes, see, e.g., Woon, *Genomics* 50: 306-316, 1998; P1-derived vectors (PACs), see, e.g., Kern, *Biotechniques* 23: 120-124, 1997; cosmids, recombinant viruses, phages or plasmids.

The invention provides fusion proteins and nucleic acids encoding them. A gene product or polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego, Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams, *Biochemistry* 34: 1787-1797, 1995; Dobeli, *Protein Expr. Purif.* 12: 404-414, 1998). The histidine residues facilitate detection and purification while the enterokinase cleavage site provides a means for purifying the epitope from the remainder of the fusion protein. In one aspect, a nucleic acid encoding a polypeptide of the invention is assembled in appropriate phase with a leader sequence capable of directing secretion of the translated polypeptide or fragment thereof. Technology pertaining to vectors encoding fusion proteins and application of fusion proteins are well described in the scientific and patent literature, see e.g., Kroll, *DNA Cell. Biol.* 12: 441-53, 1993.

Transcriptional Control Elements

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

Expression Vectors and Cloning Vehicles

The invention provides expression vectors and cloning vehicles comprising nucleic acids of the invention, e.g., sequences encoding the proteins of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus*, *Aspergillus* and yeast). See, for example, U.S. Pat. No. 5,707,855. Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair.

The invention provides libraries of expression vectors encoding polypeptides and peptides of the invention. These nucleic acids can be introduced into a genome or into the cytoplasm or a nucleus of a cell and expressed by a variety of conventional techniques, well described in the scientific and patent literature. See, e.g., Roberts, *Nature* 328: 731, 1987; Schneider, *Protein Expr. Purif.* 6435: 10, 1995; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids of the invention are administered in vivo for in situ expression of the peptides or polypeptides of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors can also be employed which exploit advantageous merits of each of the parent vector properties (See e.g., Feng, *Nature Biotechnology* 15: 866-870, 1997). Such viral genomes can be modified by recombinant DNA techniques to include the nucleic acids of the invention; and can be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immunodeficiency virus (HIV), and combinations thereof; see, e.g., U.S. Pat. Nos. 6,117,681; 6,107,478; 5,658,775; 5,449,614; Buchscher, *J. Virol.* 66: 2731-2739, 1992; Johann, *J. Virol.* 66: 1635-1640, 1992). Adeno-associated virus (AAV)-based vectors can be used to radioimmune cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada, *Gene Ther.* 3: 957-964, 1996.

"Expression cassette" as used herein refers to a nucleotide sequence which is capable of affecting expression of a structural gene (i.e., a protein coding sequence, such as a polypeptide of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression can also be used, e.g., enhancers.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination. Thus, expression cassettes also include plasmids, expression vectors, recombinant viruses, any form of recombinant "naked DNA" vector, and the like.

"Vector" is intended to refer to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Host Cells and Transformed Cells

The invention also provides a transformed cell comprising a nucleic acid sequence of the invention, e.g., a sequence encoding a polypeptide of the invention, or a vector of the invention. The host cell can be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces,* and *Staphylococcus.* Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter can be induced by appropriate means (e.g., temperature shift or chemical induction) and the cells can be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct can be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides of the invention.

Amplification methods include, e.g., polymerase chain reaction, PCR (Pcr Protocols, A Guide To Methods And Applications, ed. Innis, Academic Press, N.Y., 1990 and PCR STRATEGIES, 1995, ed. Innis, Academic Press, Inc., N.Y., ligase chain reaction (LCR) (see, e.g., Wu, *Genomics* 4: 560, 1989; Landegren, *Science* 241: 1077, 1988; Barringer, *Gene* 89: 117, 1990); transcription amplification (see, e.g., Kwoh, *Proc. Natl. Acad. Sci. USA* 86: 1173, 1989); and, self-sustained sequence replication (see, e.g., Guatelli, *Proc. Natl. Acad. Sci. USA* 87: 1874, 1990); Q Beta replicase amplification (see, e.g., Smith, *J. Clin. Microbiol.* 35: 1477-1491, 1997), automated Q-beta replicase amplification assay (see, e.g., Burg, *Mol. Cell. Probes* 10: 257-271, 1996) and other RNA polymerase mediated techniques (e.g., NASBA, Cangene, Mississauga, Ontario); see also Berger, *Methods Enzymol.* 152: 307-316, 1987; Sambrook; Ausubel; U.S. Pat. Nos. 4,683,195 and 4,683,202; Sooknanan, *Biotechnology* 13: 563-564, 1995.

Hybridization of Nucleic Acids

The invention provides isolated or recombinant nucleic acids that hybridize under stringent conditions to an exemplary sequence of the invention, e.g., a sequence or related sequence, or the complement of any thereof, or a nucleic acid that encodes a polypeptide of the invention. In alternative aspects, the stringent conditions are highly stringent conditions, medium stringent conditions or low stringent conditions, as known in the art and as described herein. These methods can be used to isolate nucleic acids of the invention.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800 or more residues in length, or, the full length of a gene or coding sequence, e.g., cDNA. Nucleic acids shorter than full length are also included. These nucleic acids can be useful as, e.g., hybridization probes, labeling probes, PCR oligonucleotide probes, iRNA, antisense or sequences encoding antibody binding peptides (epitopes), motifs, active sites and the like.

"Selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least at about 10 times background. In one embodiment, a nucleic acid can be determined to be within the scope of the invention by its ability to hybridize under stringent conditions to a nucleic acid otherwise determined to be within the scope of the invention (such as the exemplary sequences described herein).

"Stringent hybridization conditions" refers to conditions under which a probe will hybridize to its target subsequence, typically in a complex mixture of nucleic acid, but not to other sequences in significant amounts (a positive signal (e.g., identification of a nucleic acid of the invention) is about 10 times background hybridization). Stringent conditions are sequence-dependent and will be different in different circumstances. Longer sequences hybridize specifically at higher temperatures. An extensive guide to the hybridization of nucleic acids is found in, e.g., Sambrook, ed., 1989; Ausubel, ed. 1997; Tijssen, ed., 1993, supra).

Generally, stringent conditions are selected to be about 5-10° C. lower than the thermal melting point I for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide as described in Sambrook (cited below). For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. For selective or specific hybridization, a positive signal (e.g., identification of a nucleic acid of the invention) is about 10 times background hybridization. Stringent hybridization conditions that are used to identify nucleic acids within the scope of the invention include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. In the present invention, genomic DNA or cDNA comprising nucleic acids of the invention can be identified in standard Southern blots under stringent conditions using the nucleic acid sequences disclosed here. Additional stringent conditions for such hybridizations (to identify nucleic acids within the scope of the invention) are those which include a hybridization in a buffer of 40% formamide, 1 M NaCl, 1% SDS at 37° C.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g., a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

Oligonucleotides Probes and Methods for Using Them

The invention also provides nucleic acid probes for identifying nucleic acids encoding a polypeptide of interest. In one aspect, the probe comprises at least 10 consecutive bases of a nucleic acid of the invention. Alternatively, a probe of the invention can be at least about 5, 6, 7, 8, 9, 10, 15, 20, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays for drug screening, see discussion below. The probes of the invention can also be used to isolate other nucleic acids or polypeptides.

Use of Differentiated Cells

Cells prepared according to this invention can be used for a variety of commercially important research, diagnostic, and therapeutic purposes.

Because the cell populations of this invention are depleted of undifferentiated cells, they can be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000).

Relatively homogeneous cell populations are particularly suited for use in drug screening and therapeutic applications.

Drug Screening

Differentiated pPS cells of this invention can be used to screen for factors (such as solvents, small molecule drugs, peptides, polynucleotides, and the like) or environmental conditions (such as culture conditions or manipulation) that affect the characteristics of differentiated cells.

In some applications, differentiated cells are used to screen factors that promote maturation, or promote proliferation and maintenance of such cells in long-term culture. For example, candidate maturation factors or growth factors are tested by adding them to pPS cells in different wells, and then determining any phenotypic change that results, according to desirable criteria for further culture and use of the cells.

Particular screening applications of this invention relate to the testing of pharmaceutical compounds in drug research. The reader is referred generally to the standard textbook "In vitro Methods in Pharmaceutical Research", Academic Press, 1997, and U.S. Pat. No. 5,030,015). Assessment of the activity of candidate pharmaceutical compounds generally involves combining the differentiated cells of this invention with the candidate compound, determining any change in the morphology, marker phenotype, or metabolic activity of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. $^3$H thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp. 375-410 in "In vitro Methods in Pharmaceutical Research," Academic Press, 1997) for further elaboration.

Human development from ES cells to neuroectoderm/neuroepethilium (homogenous) directed differentiation in vitro abnormalities, and the like.

High Throughput Format

An assay performed in a "homogeneous format" means that the assay can be performed in a single container, with no manipulation or purification of any components being required to determine the result of the assay, e.g., a test agent can be added to an assay system and any effects directly measured. Often, such "homogeneous format" assays will comprise at least one component that is "quenched" or otherwise modified in the presence or absence of a test agent.

A "secondary screening step" refers to a screening step whereby a test agent is assessed for a secondary property in order to determine the specificity or mode of action of a compound identified using the methods provided herein. Such secondary screening steps can be performed on all of the test agents, or, e.g., on only those that are found to be positive in a primary screening step, and can be performed subsequently, simultaneously, or prior to a primary screening step.

"High throughput screening" refers to a method of rapidly assessing a large number of test agents for a specific activity. Typically, the plurality of test agents will be assessed in parallel, for example by simultaneously assessing 96 or 384 agents using a 96-well or 384-well plate, 96-well or 384-well dispensers, and detection methods capable of detecting 96 or 384 samples simultaneously. Often, such methods will be automated, e.g., using robotics.

"Robotic high throughput screening" refers to high throughput screening that involves at least one robotic element, thereby eliminating a requirement for human manipulation in at least one step of the screening process. For example, a robotic arm can dispense a plurality of test agents to a multi-well plate.

A "multi-well plate" refers to any container, receptacle, or device that can hold a plurality of samples, e.g., for use in high throughput screening. Typically, such "multi-well plates" will be part of an integrated and preferably automated system that enables the rapid and efficient screening or manipulation of a large number of samples. Such plates can include, e.g., 24, 48, 96, 384, or more wells, and are typically used in conjunction with a 24, 48, 96, 384, or more tip pipettors, samplers, detectors, and the like.

In some assays, it will be desirable to have positive controls to ensure that the components of the assays are working properly.

In the high throughput assays of the invention, it is possible to screen up to several thousand different modulators in a single day. In particular, each well of a microtiter plate can be used to run a separate assay against a selected potential modulator, or if concentration or incubation time effects are to be observed, every 5-10 wells can test a single modulator. Thus, a single standard microtiter plate can assay about 100 (96) modulators. If 1536 well plates are used, then a single plate can easily assay from about 100 to about 1500 different compounds. It is possible to assay many different plates per day; assay screens for up to about 6,000-20,000, and even up to about 100,000-1,000,000 different compounds are possible using the integrated systems of the invention.

Solid State and Soluble High Throughput Assays

The invention provides assays using the substantially pure homogeneous population of neural precursor cells or tissue espressing such cells. The invention further provides solid phase based in vitro assays in a high throughput format, where a protein of interest or fragment thereof, is attached to a solid phase substrate.

In the high throughput assays of the invention, either soluble or solid state, it is possible to screen up to several thousand different modulators or ligands in a single day. This methodology can be used for proteins in vitro, or for cell-based or membrane-based assays comprising a protein of interest. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention. For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, and the like) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, and the like), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85: 2149-2154, 1963 (describing solid phase synthesis of, e.g., peptides); Geysen et al., *J. Immun. Meth.* 102: 259-274, 1987 (describing synthesis of solid phase components on pins); Frank & Doring, *Tetrahedron* 44:60316040 (1988) (describing synthesis of various peptide sequences on cellulose disks); Fodor et al., *Science,* 251: 767-777, 1991; Sheldon et al., *Clinical Chemistry* 39(4): 718-719, 1993; and Kozal et al., *Nature Medicine* 2(7):753-759, 1996 (all describing arrays of biopolymers fixed to solid substrates). Non-chemical approaches for fixing tag binders to substrates include other common methods, such as heat, cross-linking by UV radiation, and the like.

Therapeutic Uses

The present invention concerns hNPCs and their uses, such as for research or for therapeutic uses for an animal in need thereof, such as with cell replacement therapy. The cells may be therapeutic as they were collected, or they may be manipulated prior to their application. Such manipulations may be of any kind to enhance their therapeutic activity for the individual(s) to which they are applied.

In particular embodiments, the cells of the present invention further include a therapeutic agent, such as a small molecule, therapeutic polypeptide, a nucleic acid encoding a therapeutic polypeptide, siRNA, antisense RNA, RNAi, lipids, including phospholipids, proteolipids and glycolypids, or a mixture thereof. In one embodiment, the therapeutic agent provides amelioration of at least one symptom of a medical condition, and/or prevents at least one symptom of a medical condition. The particular cells utilized in this aspect of the invention are suitable for their intended purpose. Example applications such as those that follow may be employed, although a skilled artisan recognizes other suitable applications may be utilized.

Differentiated cells of this invention can also be used for tissue reconstitution or regeneration in a human patient in need thereof. The cells are administered in a manner that permits them to graft to the intended tissue site and reconstitute or regenerate the functionally deficient area.

In one example, neural stem cells are transplanted directly into parenchymal or intrathecal sites of the central nervous system, according to the disease being treated. Grafts are done using single cell suspension or small aggregates at a density of 25,000-500,000 cells per µL (U.S. Pat. No. 5,968, 829). The efficacy of neural cell transplants can be assessed in a rat model for acutely injured spinal cord as described by McDonald et al., *Nat. Med.* 5: 1410, 1999. A successful transplant will show transplant-derived cells present in the lesion 2-5 weeks later, differentiated into astrocytes, oligodendrocytes, and/or neurons, and migrating along the cord from the lesion end, and an improvement in gate, coordination, and weight-bearing.

Certain neural progenitor cells embodied in this invention are designed for treatment of acute or chronic damage to the nervous system. For example, excitotoxicity has been implicated in a variety of conditions including epilepsy, stroke, ischemia, Huntington's disease, Parkinson's disease, amyotrophic lateral sclerosis (ALS), and Alzheimer's disease. Certain differentiated cells of this invention may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

The cells employed for a central nervous system (CNS) application comprise a nucleic acid and therapeutic agent, such as encoding interferon-beta or brain derived neurotrophic factor, which is known to be neuroprotective; alternatively, the cells harbor a therapeutic polypeptide or small molecule, for example. Other neuroprotective agents include, glial derived neurotrophic factor (GDNF), NGF, FGF, EGF, BMP, TNFα, for example, which can also be provided in the form of a polypeptide or a nucleic acid encoding the polypeptide, for example. In specific embodiments, the nucleic acid is RNAi, siRNA, or antisense RNA.

General methods of using antisense, ribozyme technology, and RNAi technology to control gene expression, or of gene therapy methods for expression of an exogenous gene in this manner are well known in the art. Each of these methods utilizes a system, such as a vector, encoding either an antisense or ribozyme transcript of a phosphatase polypeptide of the invention. The term "RNAi" stands for RNA interference. This term is understood in the art to encompass technology using RNA molecules that can silence genes. (See, for example, McManus et al., *Nature Reviews Genetics* 3: 737, 2002). In this application, the term "RNAi" encompasses molecules such as short interfering RNA (siRNA), microRNAs (mRNA), small temporal RNA (stRNA). Generally speaking, RNA interference results from the interaction of double-stranded RNA with genes.

The invention provides antisense oligonucleotides capable of binding the message encoding the polypeptide of interest, which can inhibit polypeptide synthesis by targeting mRNA. Strategies for designing antisense oligonucleotides are well described in the scientific and patent literature, and the skilled artisan can design such oligonucleotides using the novel reagents of the invention. For example, gene walking/RNA mapping protocols to screen for effective antisense oligonucleotides are well known in the art, see, e.g., Ho, *Methods Enzymol.* 314: 168-183, 2000, describing an RNA mapping assay, which is based on standard molecular techniques to provide an easy and reliable method for potent antisense sequence selection. See also Smith, *Eur. J. Pharm. Sci.* 11: 191-198, 2000.

RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

In general, a short, interfering RNA (siRNA) comprises an RNA duplex that is preferably approximately 19 basepairs long and optionally further comprises one or two single-stranded overhangs or loops. An siRNA can comprise two RNA strands hybridized together, or can alternatively comprise a single RNA strand that includes a self-hybridizing portion. siRNAs can include one or more free strand ends, which can include phosphate and/or hydroxyl groups. siRNAs typically include a portion that hybridizes under stringent conditions with a target transcript. One strand of the siRNA (or, the self-hybridizing portion of the siRNA) is typically precisely complementary with a region of the target transcript, meaning that the siRNA hybridizes to the target transcript without a single mismatch. In certain embodiments of the invention in which perfect complementarity is not achieved, it is generally preferred that any mismatches be located at or near the siRNA termini.

A further method of RNA interference in the present invention is the use of short hairpin RNAs (shRNA). A plasmid containing a DNA sequence encoding for a particular desired siRNA sequence is delivered into a target cell via transfection or virally mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression. Inhibition of protein expression by transfected siRNAs is a transient phenomenon that does not occur for times periods longer than several days. In some cases, this can be preferable and desired. In cases where longer periods of protein inhibition are necessary, shRNA mediated inhibition is preferable.

Antisense nucleic acids are generally single-stranded nucleic acids (DNA, RNA, modified DNA, or modified RNA) complementary to a portion of a target nucleic acid (e.g., an mRNA transcript) and therefore able to bind to the target to form a duplex. Typically they are oligonucleotides that range from 15 to 35 nucleotides in length but can range from 10 up to approximately 50 nucleotides in length. Binding typically reduces or inhibits the function of the target nucleic acid. For example, antisense oligonucleotides can block transcription when bound to genomic DNA, inhibit translation when bound to mRNA, and/or lead to degradation of the nucleic acid. Reduction in expression of a polypeptide can be achieved by the administration of antisense nucleic acids or peptide nucleic acids comprising sequences complementary to those of the mRNA that encodes the polypeptide. Antisense technology and its applications are well known in the art and are described in Phillips, M. I. (ed.) *Antisense Technology, Methods Enzymol,* 2000, Volumes 313 and 314, Academic Press, San Diego, and references mentioned therein. See also Crooke, S. (ed.) "Antisense Drug Technology: Principles, Strategies, and Applications" (1$^{st}$ Edition) Marcel Dekker; and references cited therein.

Antisense oligonucleotides can be synthesized with a base sequence that is complementary to a portion of any RNA transcript in the cell. Antisense oligonucleotides can modulate gene expression through a variety of mechanisms including the modulation of RNA splicing, the modulation of RNA transport and the modulation of the translation of mRNA (Denhardt, *Ann N Y Acad. Sci.* 660: 70, 1992). Various properties of antisense oligonucleotides including stability, toxicity, tissue distribution, and cellular uptake and binding affinity can be altered through chemical modifications including (i) replacement of the phosphodiester backbone (e.g., peptide nucleic acid, morpholino-oligonucleotides, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C) (Wagner, *Nat. Medicine* 1: 1116, 1995; Varga et al., *Immun. Lett.* 69: 217, 1999; Neilsen, *Curr. Opin. Biotech.* 10: 71, 1999; Woolf, *Nucleic Acids Res.* 18: 1763, 1990).

Cellular Transfection and Gene Therapy

Another aspect of the present invention is to use gene therapy methods for treating or preventing disorders, diseases, and conditions. The gene therapy methods relate to the introduction of nucleic acid (DNA, RNA and antisense DNA or RNA) sequences into an animal to achieve expression of the polypeptide or polypeptides of the present invention. This method requires one or more polynucleotides encoding a polypeptide(s) of the present invention operatively linked to a promoter and any other genetic elements necessary for the expression of the polypeptide by the target tissue.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. U.S.A.*, 83: 4143-4146, 1986). The oligonucleotides can be modified to enhance their uptake, e.g., by substituting their negatively charged phosphodiester groups by uncharged groups.

The present invention provides any nucleic acid for the transfection, transduction, or other genetic modification of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acids are under the control of a promoter(s). The compositions are administered to a patient in an amount sufficient to elicit a therapeutic response in the patient. An amount adequate to accomplish this is defined as "therapeutically effective dose or amount." Such gene therapy procedures have been used to correct acquired and inherited genetic defects, cancer, and viral infection in a number of contexts. The ability to express artificial genes in humans may facilitate the prevention and/or cure of important human diseases, including diseases which are not amenable to treatment by other therapies (for a review of gene therapy procedures, see Anderson, *Science* 256: 808-813, 1992; Nabel & Felgner, *TIBTECH* 11: 211-217, 1993; Mitani & Caskey, *TIBTECH* 11: 162-166, 1993; Mulligan, *Science* 260: 926-932, 1993; Dillon, *TIBTECH* 11: 167-175, 1993; Miller, *Nature* 357: 455-460, 1992; Van Brunt, *Biotechnology* 6(10):1149-1154, 1998; Vigne, *Restorative Neurology and Neuroscience* 8: 35-36, 1995; Kremer and Perricaudet, *British Medical Bulletin* 51: 31-44, 1995; Haddada et al., In Current Topics in Microbiology and Immunology (Doerfler & Bohm eds., 1995); and Yu, *Gene Therapy* 1: 13-26, 1994). For a review of orthopaedic gene therapy, see Evans, *Clin Orthop Relate Res* 429: 316-29, 2004 and Evans, *J. Rheumatol Suppl* 72: 17-20, 2005; general reference for mechanisms of retroviral infection, replication, and integration: Coffin, In: Retroviruses. Cold Spring Harbor Laboratory Press, Plainview, N.Y., 1997; Varmus, *Cell* 25: 23-36, 1981; Friedrich, *Methods Enzymol.* 225: 681-701, 1993; Gossler, *Science* 244: 463-5, 1989; Friedrich, *Genes Dev.* 5: 1513-23, 1991; von Melchner, *Genes Dev.* 6: 919-27, 1992; King, *Science* 228: 554-8, 1985; Hubbard, *J Biol Chem.* 269: 3717-24, 1994; these references are herein incorporated by reference for all purposes.

Nucleic acid constructs can be designed in accordance with the principles, materials, and methods disclosed in the patent documents and scientific literature cited herein, each of which is incorporated herein by reference, with modifications and further exemplification as described herein. Components of the constructs can be prepared in conventional ways, where the coding sequences and regulatory regions can be isolated, as appropriate, ligated, cloned in an appropriate cloning host, and analyzed by restriction or sequencing other convenient means. Particularly, using PCR, individual fragments including all or portions of a functional unit can be isolated, where one or more mutations can be introduced using "primer repair;" ligation, in vitro mutagenesis, and the like, as appropriate. In the case of DNA constructs encoding fusion proteins, DNA sequences encoding individual domains and subdomains can be joined such that they constitute a single open reading frame encoding a fusion protein capable of being translated in cells or cell lysates into a single polypeptide harboring all component domains. The DNA construct encoding the fusion protein can then be placed into a vector that directs the expression of the protein in the appropriate cell type(s). Alternatively, the desired DNA constructs can be generated by homologous recombination in bacteria using commercially available techniques that are well described in the literature (Zhang, *Nature Biotechnology* 18: 1314-1317, 2000). Accordingly, fusion proteins of the present invention can be generated by homologous recombination into endogenous gene loci. For biochemical analysis of the encoded chimera, it can be desirable to construct plasmids that direct the expression of the protein in bacteria or in reticulocyte-lysate or other in vitro translation systems. For use in the production of proteins in mammalian cells, the protein-encoding sequence can be introduced into an expression vector that directs expression in these cells. Expression vectors suitable for such uses are well known in the art. Various sorts of such vectors are commercially available.

Methods of non-viral delivery of recombinant constructs of the invention include, for example, lipofection, microinjection, biolistics, virosomes, liposomes, immunoliposomes, polycation or lipid:nucleic acid conjugates, naked DNA, artificial virions, and agent-enhanced uptake of DNA. Lipofection is described in, for example, U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270: 404-410, 1995; Blaese, *Cancer Gene Ther.* 2: 291-297, 1995;

Behr, *Bioconjugate Chem.* 5: 382-389, 1994; Remy, *Bioconjugate Chem.* 5: 647-654, 1994; Gao, *Gene Therapy* 2: 710-722, 1995; Ahmad, *Cancer Res.* 52: 4817-4820, 1992; U.S. Pat. Nos. 4,186,183, 4,217,344, 4,235,871, 4,261,975, 4,485,054, 4,501,728, 4,774,085, 4,837,028, and 4,946,787).

In certain embodiments, the polynucleotide constructs are complexed in a liposome preparation. Liposomal preparations for use in the present invention include cationic (positively charged), anionic (negatively charged), and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner, *Proc. Natl. Acad. Sci. USA* 84: 7413-7416, 1987, which is herein incorporated by reference); mRNA (Malone, *Proc. Natl. Acad. Sci. U.S.A.* 86: 6077-6081, 1989, which is herein incorporated by reference); and purified transcription factors (Debs, *J. Biol. Chem.* 265: 10189-10192, 1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner, *Proc. Natl. Acad. Sci. U.S.A.* 84: 7413-7416, 1987), which is herein incorporated by reference). Other commercially available liposomes include transfectace (DDAB/DOPE) and DOTAP/DOPE (Boehringer now part of Roche).

Other cationic liposomes can be prepared from readily available materials using techniques well known in the art. See, e.g., PCT Publication No. WO 90/11092 (which is herein incorporated by reference) for a description of the synthesis of DOTAP (1,2-bis(oleoyloxy)-3-(trimet-hylammonio)propane) liposomes. Preparation of DOTMA liposomes is explained in the literature, see, e.g., Felgner, *Proc. Natl. Acad. Sci. U.S.A.* 84: 7413-7417, 1987, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidy, choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with the DOTMA and DOTAP starting materials in appropriate ratios. Methods for making liposomes using these materials are well known in the art.

For example, commercial dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is maintained at 15° C. Alternatively, negatively charged vesicles can be prepared without sonication to produce multilamellar vesicles or by extrusion through nucle-opore membranes to produce unilamellar vesicles of discrete size. Other methods are known and available to those of skill in the art.

The liposomes can comprise multilamellar vesicles (MLVs), small unilamellar vesicles (SUWs), or large unilamellar vesicles (LUVs), with SUVs being preferred. The various liposome-nucleic acid complexes are prepared using methods well known in the art. See, e.g., Straubinger, *Methods of Immunology* 101: 512-527, 1983, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LU~s are prepared by a number of methods, well known in the art. Commonly used methods include $Ca^{2+}$-EDTA chelation (Papahadjopoulos, *Biochim. Biophys. Acta* 394: 483, 1975; Wilson, *Cell* 17: 77, 1979; ether injection (Deamer, *Biochim. Biophys. Acta* 443: 629, 1976; Ostro, *Biochem. Biophys. Res. Commun.* 76: 836, 1977; Fraley, *Proc. Natl. Acad. Sci. U.S.A.* 76: 3348, 1979; detergent dialysis (Enoch, *Proc. Natl. Acad. Sci. U.S.A.* 76: 145, 1979, and reverse-phase evaporation (REV) (Fraley, *J. Biol. Chem.* 255: 10431, 19806; Szoka and Papahadjopoulos, *Proc. Natl. Acad. Sci. U.S.A.* 75: 145, 1978; and Schaefer-Ridder, *Science* 215: 166, 1982), which are herein incorporated by reference.

Generally, the ratio of DNA to liposomes will be from about 10:1 to about 1:10. Preferably, the ratio will be from about 5:1 to about 1:5. More preferably, the ratio will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

The use of RNA or DNA viral based systems for the delivery of recombinant constructs encoding fusion proteins of the invention can take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of constructs of the invention include, but are not limited to, retrovirus, lentivirus, human foamy virus, adenovirus, adeno-associated virus (AAV), adeno-AAV, and herpes simplex virus vectors for gene transfer. Viral vectors are currently the most efficient and versatile method of gene transfer in target cells and tissues. Integration in the host genome is possible with the retrovirus, human foamy virus, lentivirus, and adeno-associated virus gene transfer methods, often resulting in long-term expression of the inserted transgene. Additionally, high transduction efficiencies have been observed in many different cell types and target tissues.

The tropism of a retrovirus can be altered by incorporating foreign envelope proteins, expanding the potential target population of target cells. Pseudotypes that are well suited for the transduction of human hematopoietic cells can include the envelopes of gibbon ape leukemia virus (GaLV) (Horn, *Blood* 100: 3960-7, 2002) and endogenous feline leukemia virus (RD114) (Neff, *Mol. Ther.* 9: 157-9, 2004). Virus production can be achieved using murine or human packaging cell lines. Lentivirus vectors and human foamy virus vectors are retroviral vectors that are able to transduce or infect non-dividing cells and typically produce high viral titers. Selection of a retroviral gene transfer system would therefore depend on the target tissue. Retroviral vectors are generally comprised of cis-acting long terminal repeats with packaging capacity for up to 6-10 kb of foreign sequence. The minimum cis-acting LTRs are sufficient for replication and packaging of the vectors, which are then used to integrate a construct into the target cell to provide permanent transgene expression. Widely used retroviral vectors include those based upon murine leukemia virus (MuLV), Simian Immuno deficiency virus (SIV), human immuno deficiency virus (HIV), human foamy virus, and combinations thereof (see, e.g., Buchscher, *J. Virol.* 66: 2731-2739, 1992; Johann, *J. Virol.* 66: 1635-1640, 1992; Sommerfelt, *Virol.* 176: 58-59, 1990; Wilson, *J. Virol.* 63: 2374-2378, 1989; Mergia and Heinkelein, *Curr Top Microbiol Immunol.* 277: 131-59, 2003, Miller, *J. Virol.* 65: 2220-2224, 1991; PCT/US94/05700).

Methods for using oncoretrovirus, lentivirus, or human foamy virus vectors for transfer of the fusion protein of the present invention into various cell types, including hematopoietic stem cells, are well described in the literature (reviewed in Brenner and Malech, *Biochim Biophys Acta.* 1640: 1-24, 2003). Hematopoietic stem cells can be obtained by isolating mononuclear cells from the bone marrow or from the peripheral blood, the latter most commonly done using leukapheresis. In most cases, collection of peripheral blood mononuclear cells is performed following several days of G-CSF administration, which acts to mobilize stem cells from the bone marrow to the blood. Hematopoietic stem cells can be enriched from mononuclear cell collections using either positive selection systems (most commonly based on the expression of CD34) or negative selection systems, resulting in the depletion of cells expressing lineage specific cell surface markers. Populations enriched in stem cells can then be subjected to gene transfer. In the case of oncoretrovirus vectors, hematopoietic cells undergo a period of "prestimulation", during which they are cultured in the presence of a combination of growth factors (usually including stem cell factor, IL-6, thrombopoietin, and flt-3 ligand), most commonly for a period of 48 hours. Gene transfer is commonly accomplished by preloading retrovirus supernatant on retronectin-coated dishes, and then culturing the cells in retrovirus supernatant in the presence of the same or similar combination of cytokines as used during the prestimulation step. Cultures in the presence of retroviral supernatant are typically performed over a period of 48 hours, with 2 or more changes of retroviral supernatant during the culture period. In contrast to oncoretroviral vectors, gene transfer using lentivirus or human foamy virus vectors can commonly be performed overnight without added growth factors. The fewer ex vivo manipulations associated with use of lentivirus or human foamy virus vectors can improve the engraftability of hematopoietic stem cells transduced with these vectors.

Transduced human neural precursor cells can have an engraftment defect following transplantation. While many myeloablative conditioning regimens have been described, these are encumbered by toxicity, and it is desirable to employ treatments that facilitate the engraftment of transduced hematopoietic stem cells while minimizing toxicity to the patient. A number of attenuated conditioning regimens that facilitate the engraftment of autologous or allogeneic donor stem cells, have been devised (reviewed in Georges and Storb, *Int J Hematol.* 77: 3-14, 2003). These include the administration of fludarabine and low doses of radiation therapy (typically 200 cGy) (Maris and Storb, *Immunol Res.* 28: 13-24, 2003). Busulfan administration has been used successfully to facilitate the engraftment of transduced autologous hematopoietic stem cells. (Aiuti, *Int J Hematol.* 77: 3-14, 2003). Additionally, cells can be genetically modified or otherwise treated to facilitate their engraftment, for example by inhibiting the function of the surface membrane protein, CD26 (Christopherson, *Science* 305: 1000-3, 2004).

In applications where transient expression of the fusion protein of the invention is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with the recombinant constructions, (see, e.g., West, *Virology* 160: 38-47, 1987; U.S. Pat. No. 4,797,368; WO 93/24641; Kotin, *Human Gene Therapy* 5: 793-801, 1994; Muzyczka, *J. Clin. Invest.* 94: 1351, 1994. Construction of recombinant AAV vectors are described in a number of publications, including U.S. Pat. No. 5,173,414; Tratschin, *Mol. Cell. Biol.* 1985, 5: 3251-3260; Tratschin, *Mol. Cell. Biol.* 4: 2072-2081, 1984; Hermonat and Muzyczka, *Proc. Natl. Acad. Sci. U.S.A.* 81: 6466-6470, 1984; and Samulski, *J. Virol.* 63: 3822-3828, 1989).

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is about 4.4 kb. The following are examples of proteins have been expressed using various AAV-based vectors, and a variety of promoter/enhancers: neomycin phosphotransferase, chloramphenicol acetyl transferase, Fanconi's anemia gene, cystic fibrosis transmembrane conductance regulator, and granulocyte macrophage colony-stimulating factor (see Table 1 in Kotin, *Human Gene Therapy* 5: 793, 1994). A transgene incorporating the various constructs of this invention can similarly be included in an AAV-based vector. As an alternative to inclusion of a constitutive promoter such as CMV to drive expression of the recombinant DNA encoding the fusion protein(s), an AAV promoter can be used (ITR itself or AAV p5 (Flotte, *J. Biol. Chem.* 268: 3781, 1993).

Such a vector can be packaged into AAV virions by reported methods. For example, a human cell line such as 293 can be co-transfected with the AAV-based expression vector and another plasmid containing open reading frames encoding AAV rep and cap under the control of endogenous AAV promoters or a heterologous promoter. In the absence of helper virus, the rep proteins Rep68 and Rep78 prevent accumulation of the replicative form, but upon superinfection with adenovirus or herpes virus, these proteins permit replication from the ITRs (present only in the construct containing the transgene) and expression of the viral capsid proteins. This system results in packaging of the transgene DNA into AAV virions (Carter, *Current Opinion in Biotechnology* 3: 533, 1992; Kotin, *Human Gene Therapy* 5: 793, 1994). Methods to improve the titer of AAV can also be used to express the transgene in an AAV virion. Such strategies include, but are not limited to: stable expression of the ITR-flanked transgene in a cell line followed by transfection with a second plasmid to direct viral packaging; use of a cell line that expresses AAV proteins inducibly, such as temperature-sensitive inducible expression or pharmacologically inducible expression. Additionally, the efficiency of AAV transduction can be increased by treating the cells with an agent that facilitates the conversion of the single stranded form to the double stranded form, as described in Wilson, et al. W096/39530. AAV vectors have been used to direct homologous recombination so that genes can be modified at their endogenous loci (Hirata, *Nat Biotechnol.* 20: 735-8, 2002). Using this or other approaches for homologous recombination, novel proteins can be generated, for example, by inserting sequences encoding the ligand binding-domain directly adjacent to endogenous genetic sequences encoding a signaling domain of interest. Alternatively, in some embodiments, sequences encoding a desired signaling domain can be inserted adjacent to an endogenously expressed ligand-binding domain.

Concentration and purification of the virus can be achieved by reported methods such as banding in cesium chloride gradients, as was used for the initial report of AAV vector expression in vivo (Flotte, *J. Biol. Chem.* 268: 3781, 1993) or chromatographic purification, as described in O'Riordan, et al. W097/08298.

For additional detailed guidance on AAV technology which can be useful in the practice of the subject invention, including methods and materials for the incorporation of a transgene, the propagation and purification of the recombinant AAV vector containing the transgene, and its use in transfecting cells and mammals, see e.g., U.S. Pat. Nos. 4,797,368; 5,139,941; 5,173,414; 5,252,479; 5,354,678; 5,436,146; 5,454,935; 5,658,776 and WO 93/24641.

pLASN and MFG-S are examples of retroviral vectors that have been used in clinical trials (Dunbar, *Blood* 85: 3048-305, 1995; Kohn, *Nat. Med.* 1: 1017-102, 1995; Malech, *Proc. Natl. Acad. Sci. U.S.A.* 94: 12133-12138, 1997). PA317/pLASN was the first therapeutic vector used in a gene therapy trial. (Blaese, *Science* 270: 475-480, 1995). Transduction efficiencies of 50% or greater have been observed for MFG-S packaged vectors. (Ellem, *Immunol Immunother.* 44: 10-20, 1997; Dranoff, *Hum. Gene Ther.* 1: 111-2, 1997).

Recombinant adeno-associated virus vectors (rAAV) are promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner, *Lancet* 351: 1702-3, 1998, Kearns, *Gene Ther.* 9: 748-55, 1996).

Replication-deficient recombinant adenoviral vectors (Ad) can be engineered such that a transgene replaces the Ad E1a, E1b, and E3 genes; subsequently the replication defective vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman, *Hum. Gene Ther.* 7: 1083-9, 1998. Additional examples of the use of adenovirus vectors for gene transfer in clinical trials include Rosenecker, *Infection* 24: 5-10; Sterman, *Hum. Gene Ther.* 9: 1083-1089, 1998; Welsh, *Hum. Gene Ther.* 2: 205-18, 1995; Alvarez, *Hum. Gene Ther.* 5: 597-613, 1997; Topf, *Gene Ther.* 5: 507-513, 1998; Sterman, *Hum. Gene Ther.* 7: 1083-1089, 1998.

Packaging cells can be used to form virus particles that are capable of infecting a host cell. Such cells include 293 cells, which package adenovirus, and $\psi$2 cells or PA317 cells, which package retrovirus. Viral vectors used in gene therapy are usually generated by producer cell lines that package nucleic acid vectors into viral particles. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome, which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment, to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the virus' outer surface. The ligand is chosen to have affinity for a receptor known to be present on the cell type of interest. For example, Han, *Proc. Natl. Acad. Sci. U.S.A.* 92: 9747-9751, 1995, reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, often after selection for cells that have incorporated the vector.

Ex vivo cell transfection for research or for gene therapy (e.g., via re-infusion of the transfected cells into the host organism) is well known to those of skill in the art. In some embodiments, cells are isolated from the subject organism, transfected with a recombinant construct encoding a fusion protein of the invention, and re-infused back into the subject mammal (e.g., patient). Various cell types suitable for ex vivo transfection are well known to those of skill in the art (see, e.g., Freshney, Culture of Animal Cells, A Manual of Basic Technique (3rd ed. 1994)) and the references cited therein for a discussion of how to isolate and culture cells from patients).

The cellular compositions of the invention can be used in ex vivo procedures for cell transfection and gene therapy. The advantage to using the cellular compositions is that they can be differentiated into other cell types in vitro, or can be introduced into a mammal (such as the donor of the cells) where they will engraft.

Vectors (e.g., retroviruses, adenoviruses, liposomes, and the like) containing therapeutic nucleic acids can also be administered directly to the organism for transduction of cells in vivo. Alternatively, naked DNA can be administered. In one embodiment, the polynucleotide of the present invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotide of the present invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs used in the gene therapy method are preferably constructs that will not integrate into the host genome nor will they contain sequences that allow for replication. Appropriate vectors include pWL-NEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of the polynucleotide sequence. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the β-actin promoter; and human growth hormone promoters. The promoter also can be the native promoter for the polynucleotide of the present invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue (including synovial membrane, joint capsule, and perichondrium). Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels or the intraarticular space within synovial joints. Delivery to the interstitial space of muscle tissue is preferred for the reasons discussed below. They can be conveniently delivered by injection into the tissues comprising these cells. They are preferably delivered to and expressed in persistent, non-dividing cells that are differentiated, although delivery and expression can be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and can depend on the condition being treated and the route of administration.

The preferred route of administration is by the parenteral route of injection into the interstitial space of tissues. However, other parenteral routes can also be used, such as, inhalation of an aerosol formulation particularly for delivery to lungs or bronchial tissues, throat, or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs can also be delivered with delivery vehicles such as viral sequences, viral particles, liposome formulations, lipofectin, precipitating agents, and the like. Such methods of delivery are known in the art.

Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Generally, the DNA or viral particles are transferred to a biologically compatible solution or pharmaceutically acceptable delivery vehicle, such as sterile saline, or other aqueous or non-aqueous isotonic sterile injection solutions or suspensions, numerous examples of which are well-known in the art, including Ringer's, phosphate buffered saline, or other similar vehicles.

Preferably, the DNA or recombinant virus is administered in sufficient amounts to transfect or transduce cells at a level providing therapeutic benefit without undue adverse effects.

Any of these techniques can also be applied to introducing a transcriptional regulatory sequence into cells or population of cells to activate a desired endogenous gene. This can be done by both homologous (e.g., U.S. Pat. No. 5,641,670) or non-homologous (e.g., U.S. Pat. No. 6,602,686) recombination. These are incorporated by reference for teaching of methods of endogenous gene activation.

The invention provides uses of the substantially pure homogeneous neural precursor cell composition for the preparation of a medicament for treatment of neuronal and related diseases. In some aspects, certain neural progenitor cells embodied in this invention are designed for treatment of acute or chronic damage to the nervous system. A variety of conditions can include epilepsy, stroke, ischemia, Huntington's disease, Parkinson's disease, amyotrophic lateral sclerosis (ALS), and Alzheimer's disease. Certain differentiated cells of this invention may also be appropriate for treating dysmyelinating disorders, such as Pelizaeus-Merzbacher disease, multiple sclerosis, leukodystrophies, neuritis and neuropathies.

In another aspect, the invention provides uses of the substantially pure homogeneous neural precursor cell composition in human cell therapy and gene therapy. In some aspects, certain neural progenitor cells embodied in this invention are designed for treatment of acute or chronic damage to the nervous system. A variety of conditions can include epilepsy, stroke, ischemia, Huntington's disease, Parkinson's disease, amyotrophic lateral sclerosis (ALS), and Alzheimer's disease. Certain differentiated cells of this invention may also be appropriate for treating dysmyelinating disorders, such as Pelizaeus-Merzbacher disease, multiple sclerosis, leukodystrophies, neuritis and neuropathies.

Kits

In specific embodiments of the present invention, there are one or more kits for making and/or using the hNPCs and resulting differentiated cells of the invention. The components of the kit are housed in a suitable container and may be sterile, where appropriate. Kit housing may include boxes, vials, or bottles, for example.

The kit may include the suitable media or ingredients thereof, and in some embodiments the media is serum-free, whereas in other embodiments the media comprises serum. The kit may include one or more containers for culturing of the cells, and it may further include a transfer means, such as pipettes, for transferring the suspended cells. In other embodiments, there are components for application of the stem cells to an individual, such as a syringe, a filter for concentrating the cells, an aqueous solution for suspension of the cells, a needle, a syringe, and so forth. A therapeutic product can include sterile saline or another pharmaceutically acceptable emulsion and suspension base as described above.

Kits of the present invention can also contain additional agents that can be administered concomitantly with the compounds of the present invention. In addition, kits can contain reagents or other components used to phenotype hNPCs.

In addition, the kits can include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips, and the like), optical media (e.g., CD ROM), and the like. Such media can include addresses to internet sites that provide such instructional materials.

The examples that follow are provided by way of further illustration, and are not meant to imply any limitation in practicing the claimed invention.

EXAMPLES

Materials and Methods

Cell cultures. Two NIH-approved human ES cell lines (H9 and H14), were used with equal success to generate homogeneous cultures of human neural precursors. For the in vitro studies, H9 cells transduced with the lentivirus harboring OCT4-EGFP cassette was used. hESCs were grown on growth factor reduced matrigel (BD Biosciences) on Murine Embryonic Fibroblasts (MEFs) feeders in knockout DMEM-20% serum replacement and 8 ng/ml bFGF. For expansion, H9 cells were split using collagenase-IV every 6-7 days. For NPCs derivation hES cell colonies were collected 4 days after plating, gently triturated and washed twice with PBS.

Spheroid bodies formation: the small clusters (10-100 cells) of hESCs were grown in polypropylene dishes (Ted Pella) in Suspension Medium (1:1 ratio of DMEM/F12:neurobasal medium with N2+B27 supplements, 20 ng/ml insulin 20 ng/ml bFGF, 20 ng/ml EGF and 2 mM N-acetyl cysteine (NAC)). The spheres were grown for 4-6 days, with a change in medium every alternate day. Spheres were collected, gently triturated and plated on ornithin coated (5 ng/ml, Sigma) plates (Corning) in the hNPCs Expansion Medium (DMEM/F12, 10% BIT 9500, 20 ng/ml bFGF, 20 ng/ml EGF, 5 µg/ml fibronectin, 2 µg/ml heparin) for another 4 days to obtain the monolayers of hES-NPCs.

Hunan brain-derived NPCs (hNPC). The derivation and characterization of human brain-NPCs was previously described (Palmer et al., Nature 411: 42-3, 2001; Schwartz et al., J Neurosci Res 74: 838-51, 2003). Cells were received from Dr. Phillip Schwartz and maintained under conditions identical to that of used to expand hES-NPCs for 3 passages before using for experiments.

In vitro differentiation. hES-NPCs cells were plated on the ornithin (100 ng/ml, 1 hr at RT or 4 degrees overnight)+laminin (5 ng/ml, 1 hr at 37° C.)–coated cover slips in differentiation medium (DMEM F12 with B27 supplement containing 1% horse serum or DMEMF12:Neurobasal medium; 3:1 with 1×B27) and cultured for 7-14 days before fixation and antibody staining or 2-5 weeks for electrophysiological studies.

Immunochistochemistry. Glass cover slips were prepared by washing in water and incubating in 65% nitric acid for 1-2 days. Subsequently, cover slips were floated in water for several hours, rinsed in ethanol, air-dried and sterilized under the UV light. Cells were fixed with freshly prepared, ice cold 4% paraformaldehyde (PFA) for 10 min, washed in PBS and blocked for 1 h in blocking buffer PBTx (0.5% BSA, 1% triton X-100 in 1×PBS). Cells were incubated with Primary antibodies against OCT4, SOX2, NESTIN, MUSASHI, VIMENTIN, GFAP, O1, O4, TUJ1, MAP2, MBP, NSE, over night at 4° C. All Primary antibodies used in this study are from Chemicon except anti-OCT4(santa cruz) and anti-TUJ1 (Covance). Stained cells were mounted in AquaPoly/Mount (Polysciences).

RT-PCR. Undifferentiated hESCs, clusters growing in suspension medium for 6 days and hNPC's grown for an additional 5-6 days in expansion medium were collected and lysed in Trizol (Sigma) for RNA isolation. 2 ug of total RNA of each was used for reverse transcription according to manufacturer specification (Invitrogen). The RT product was diluted ten fold prior to PCR amplification with gene specific primers (supplementary materials).

Lentiviral Transduction. A single cell suspension of hNPC's was prepared by incubation in $Ca^{2+}$ and $Mg^{2+}$ free PBS for 15 minutes. The cells were collected in a 5 ml polystyrene tube and resuspended in 500 ul of expansion medium containing 5 ug/ml polybrene and $2^{nd}$ generation p156-RRL-sin18-PPT-hPGK-EGFP-PRE lentivirus ((Naldini and Verma, 2000) at an MOI of 5. The cells within the tube were incubated at 37° C., 5% $CO_2$ for 3 hrs. The cells were then washed with PBS prior to plating in expansion medium on ornithin coated plates. Approximately 70% GFP positive cells were detected 24 hrs post infection. For the in vitro studies, H9 cells transduced with the lentiviruses harboring tissue specific promoter-reporter cassettes were used (Oct4-GFP, Musashi1-EGFP and MELK-EGFP).

Proteome profiling. Cells were washed with ice-cold PBS lysed in Triton X (TX)-100 lysis buffer (0.2% (w/v) TX-100, 20 mM HEPES, 80 mM β-glycerophosphate, 200 mM EGTA, 15 mM $MgCl_2$, 1 mM $Na_3VO_4$, 1 mM phenylmethyl sulfonyl fluoride, 10 μg aprotinin, 10 mg/ml leupeptin (pH 7.4)) in the presence of protease inhibitors (Roche Biochemicals). About $4 \times 10^6$ cell were lysed on ice for 30-210 min and then sonciated five times for 4 s on ice. The supernatant (14,000×g at 4° C. for 10 min) was recovered and aliquots were stored at −80° C. until analyzed. The cell lysates were quickly thawed and proteins were denatured by addition of 4 volume parts of 9.5 M urea+2% CHAPS for 10 min at room temperature. Thereafter, the mixtures were spun for inorder to remove any insoluble protein. After centrifugation (10 min at 14,000×g), the supernatant (2.5, 5 or 25 μl equal to 1, 2 or 4 μg total cell protein) was mixed with 150 μl of 10 mM ammonium acetate, pH 6, containing 0.1% TX-100 for a 30 min incubation with a ProteinChip (WCX2) in a bioprocessor (Ciphergen Biosystems, Inc., Fremont, Calif., USA) on a shaker at 550 rpm. The proteinchips were washed three times with 10 mM ammonium acetate, pH 6, containing 0.1% TX-100 followed by three washes with double-distilled water. After drying on air, saturated sinapinic acid in 50% acetonitrile, 0.5% trifluor-acetic acid was applied as matrix twice at 1 μl per spot. The air-dried chip was read in a Ciphergen PBSII ProteinChip reader with the laser intensities set at 220, 240 or 260 and the detector sensitivity set to 9. The raw spectra were processed using the ProteinChip Software, version 3.1 (Ciphergen Biosystems, Inc., Fremont, Calif., USA).

hES-NPCs transplantations. Newborn ICR-CD1 pups were cryoanesthesized and 100.000 GFP infected hNPC's were injected into the left ventricle. All the pups developed normally and no tumors were detected. The animals were sacrificed at 10, 12 or 16 weeks. The heart was exposed and perfused with 30 ml of heparinized PBS followed with 30 ml of ice cold 4% paraformaldehyde. The brain was dissected out and further fixed in 4% PFA overnight, washed in PBS and saturated with 25% sucrose for 24 hrs prior to freezing in OCT. The 14 micron thick cryosections were then analysed for cells expressing GFP marker. The counter staining with anti-GFP antibody was performed as described above.

Teratoma formation assay. About $3 \times 10^6$ hESCs and hES-NPCs were injected subcutaneously or into the rear leg muscles of 4-week-old male SCID-beige mice as previously described (Thomson et al., Science 282: 1145-7, 1998).

Calcium Imaging. Calcium Imaging. Measurement of intracellular free Ca2+ ([Ca2+]i) in differentiated HNSC cultures was performed using Fura-2-AM or Fluo-3-AM as described earlier (Tenneti et al., *J Neurochem* 71: 946-59, 1998) with the minor modification. Briefly, ES derived hNPC cells were washed twice with recording medium containing 150 mM NaCl, 3 mM KCl, 2 mM CaCl2, 5 mM glucose, 10 μM glycine, and 10 mM HEPES (pH 7.4) and incubated generally at 37° C. in recording medium containing 30 nM Pluronic F-127 and 5 μM Fluo-3 AM for 30 minor 10 μMFura-2-AM for 60 min (acetoxymethyl esters; Molecular Probes). Cultures were then washed three times with recording medium, followed by settlement at 37° C. for at least 30 min. Cells were invariably used within 1 hr after these procedures for observation. During the experiments, cells were kept in a perfusion chamber on the microscope stage at room temperature (Fluo-3) or 37° C. (Fura-2 experiments). Imaging was done using a Sutter DG-4 fast wavelength switcher coupled to a Zeiss Axiovert microscope with a 20×, 0.5 NA, objective. Digital images were acquired every 500 ms with a cooled ccd camera (Cooke Sensicam, PCO, Germany) controlled by SlideBook software (Intelligent Imaging Innovations, Santa Monica, Calif.). Changes in fluorescence intensity were calculated by dividing the measured fluorescence intensity (F; ratio of 340/380 nm for Fura-2) by the measured average baseline fluorescence intensity (F/F0) Excitation was achieved using standard FITC or Fura-2 filter sets (Chroma technologies).

Electrophysiological recordings. Cultured human neural precursor cells, plated on ornithin (5 ng/ml, Sigma) glass 12 mm cover slips were placed in the recording chamber with volume about 150 μl. Recording chamber was mounted on the stage of a Zeiss Axiovert inverted microscope. The whole-cell configuration of the patch-clamp technique was used for recording macroscopic currents at room temperature (22±1° C.). Signals were amplified using Axopatch200B (Axon Instruments) amplifier, filtered below 2 KHz via Bessel low pass filter. Data were sampled and analyzed using pClamp9 software (Axon Instruments, USA) and Dell computer Pentium III in conjunction with DigiData interface (1322A, Axon Instruments, USA). The patch pipettes were pulled from the standard wall glass 1.5 mmOD (Warner) with resistance 7-10 MΩ. For the recording of voltage-gated currents we used the following composition of the intacellular solution (in mM): 140 K-gluconate; 5 NaCl, 1 $MgCl_2$; 10 EGTA; 10 HEPES, EGTA, pH adjusted by KOH to 7.25, Osmolarity was 290 mOsm. For the recording of ligand-gated currents we used this composition of intracellular solution (in mM): 130 Cs-gluconate; 2 MgATP, 1 $MgCl_2$; 10 EGTA; 10 HEPES, pH adjusted by CsOH to 7.25, Osmolarity was adjusted to 300 mOsm by sucrose solution. The bath solution generally contained a Na saline, based upon Hanks' balanced salt solution (in mM): 137 NaCl; 1 $NaHCO_3$; 0.34 $Na_2HPO_4$; 2.5 KCl; 0.44 $KH_2PO_4$; 2.5 $CaCl_2$; 0.5 $MgSO_4$; 0.5 $MgCl_2$; 5 HEPES; 22.2 glucose; pH was adjusted to 7.3 by NaOH. For the initiation voltage-gated currents we used voltage steps from −60 to +30 mV, with Δ10 mV, the duration of each step was 100 ms. Every step was initiated after hyperpolarization to −90 mV for 300 ms. The solutions of the agonists and antagonists of the different receptors were prepared on bath solution, and applied by an array of tubes placed on 50-75 μm from the cells. Solutions changes were achieved rapidly, within 50-100 msec, by moving the array of constantly flowing pipette tips relative to the cell with micromanipulator driver. A control pipette containing bath solution was used to wash applied drugs rapidly. Majority of used compounds (N-methyl-D-aspartate (NMDA), Glycine, D-2-amino-5-phosphonovalerate (D-APV), tetrodotoxin (TTX)) was purchased from Tocris (USA); γ-amino-n-butyric acid (GABA) was purchased from Sigma (USA).

Cuprizone-induced Demyelination. C57B1/6 mice were fed cuprizone (0.2% w/w; biscyclohexanoneoxaldihydrazone, Sigma) in powdered rodent lab chow for a period of four consecutive weeks as described previously 5. Two weeks following the initiation of the cuprizone diet mice were injected intravenously into the tail vein with either 100 μl of phosphate buffered saline (0.01 M) or an equivalent volume containing $5 \times 10^5$ hNPCs. Mice were kept on the cuprizone diet for an additional two weeks following stem cell administration (or vehicle). At the four week time point where cuprizone-induced demyelination was maximal, brains were extracted following halothane overdose and fixed in 10% formalin. Three micron thick parafin embedded coronal brain tissue sections were then stained for Luxol Fast Blue-PAS using a standard protocol. Adjacent sections were processed for immunohistochemical detection of dsRed using polyclonal antisera (1:2000; BD Biosciences) that was visualized using Vectastain immunohistochemistry kits with diaminobenzidine as the chromagen, according to the manufacturer's instructions.

Results

Derivations of neural precursors from hESCs. We have found that differentiating cells in human ES cell cultures promote spontaneous differentiation of pristine ES cells. To maximize the outcome of desired neural fates, we minimized the numbers of spontaneously differentiated cells in hESCs cultures prior to beginning of neural differentiation. The quality of hESCs was constantly monitored using hESCs subclone engineered with OCT4→EGFP promoter-reporter (supplementary info) (FIG. 1A insert). Routinely 90-95% of hESCs were EGFP-positive by FACS.

The undifferentiated hES cell colonies growing on MEFs (FIG. 1A) were collected 4 days after plating by gentle collagenase-IV treatment. The hES cell clusters were allowed to settle in 15 ml conical tubes for 3-5 minutes. The supernatant containing floating single cells including MEFs, differentiating cells, and some hESCs) was discarded. The sedimented clusters were then gently triturated to dislodge the loosely attached differentiating cells and to further reduce the clumps size and then washed twice with PBS. This washing step is crucial and is used in our protocol in lieu of ES cell passaging on gelatin/matrigel. The resulting hES clusters (10-100 cells) were then allowed to form spheroid bodies grown in suspension in N2/B27 medium supplemented with N-acetyl-cysteine (NAC) NAC, bFGF, and EGF. The clusters rounded up and were allowed to grow as spheres for 4-6 days, with a change in medium every alternate day (FIG. 1B). The spheres growing in suspension were collected, gently triturated and then plated on ornithin coated plates in hES-NPC expansion medium, containing bFGF and EGF. The clusters attached and appeared to be entirely composed of rosettes, with bipolar/triangular cells radiating out (FIG. 1C). After 4 days in the expansion medium hES-NPCs were replated in the same medium, forming a monolayer cultures of hES-NPCs (FIG. 1D).

Figure 2:
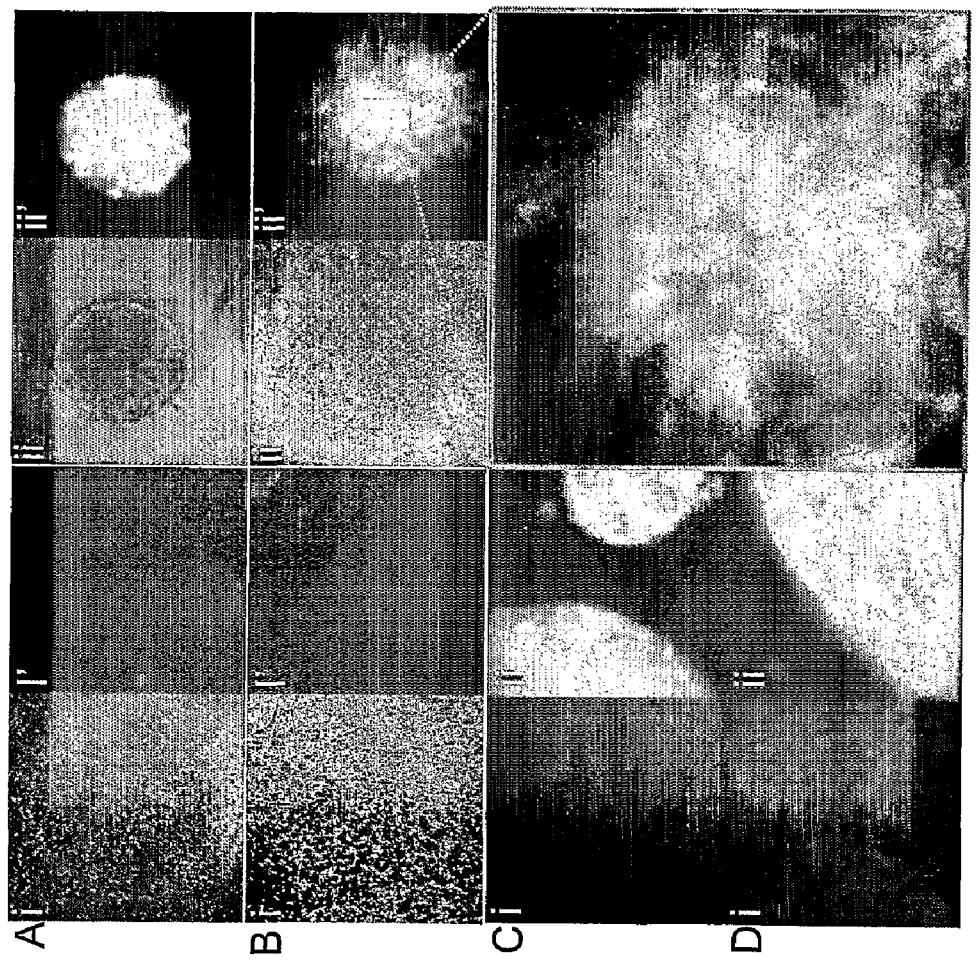
FIG. 2. Direct monitoring of hES-NPCs transition. Individual undifferentiated hES colonies (H9) infected with Musashi1→GFP (A, B) or Melk→GFP(C, D) lentivirus were manually dissected and transferred either to hES expansion medium (i/i') or neural differentiation medium (ii/ii'). The undifferentiated hESCs (Ai-Di) do not express the Musashi1 reporter (Ai', Bi') and showed barely detectable expression of the Melk reporter (Ci, Di). However, both promoters are strongly upregulated upon differentiation into neural precursor cells (A, B ii'; C, D ii), forming multiple rosettes clearly marked by GFP fluorescence (bright fields, light grey or white (insert). The bright fields in A, B correspond to the juxtaposed GFP fluorescene fields. The NPCs fluorescence appears heterogeneous in part due to the uneven cell density in sphere and the incomplete lentiviral infection.

To directly monitor hES-NPCs transition we have used promoter-reporter combination including previously characterized Musashi1 promoter, which is active in human neural precursor cells (Good et al., *Genomics* 52: 382-384, 1998; Keyoung et al., *Nat. Biotechnol.* 19: 843-850, 2001; Aubert et al., *Proc Natl Acad Sci USA* 100(1): 11836-41, 2003), as well as the MELK promoter, which was shown recently to label neural precursors both in vitro and in vivo (Nakano et al., *J Cell Biol* 170: 413-27, 2005). For this experiment we have infect hESCs with lentiviruses harboring Musashi1→GFP or MELK→GFP reporter constructs. After three passages, each colony was split and one half was continued under the hESCs growing conditions where second half was exposed to the neural differentiation conditions (FIG. 2). As expected, low or no fluorescence (of the reporters was observed in undifferentiated hESCs (FIGS. 2 Ai', Bi', Ci, Di). However, both promoters were strongly upregulated upon transfer into neural differentiation medium (FIGS. 2 A, B ii'; C, D ii). The merged rosettes of columnar neuroepithelium previously identified morphologically and by staining with Nestin and Musashi1 (Zhang et al., *Nat Biotechnol* 19: 1129-33, 2001) were clearly identifiable in differentiating cultures by EGFP fluorescence (FIG. 2 Bii' insert). The observed mosaic fluorescence is due to incomplete (80-90%) transduction of hESCs with lentiviruses. Although most known as markers of neural precursors, the expression of both Musashi1 and MELK genes is not restricted to neural lineages in vivo /REFs/. However, our gene expression and histochemical analysis (below), corroborate the idea of quantitative neuroepithelium differentiation of hESCs under the described conditions.

Figure 3:
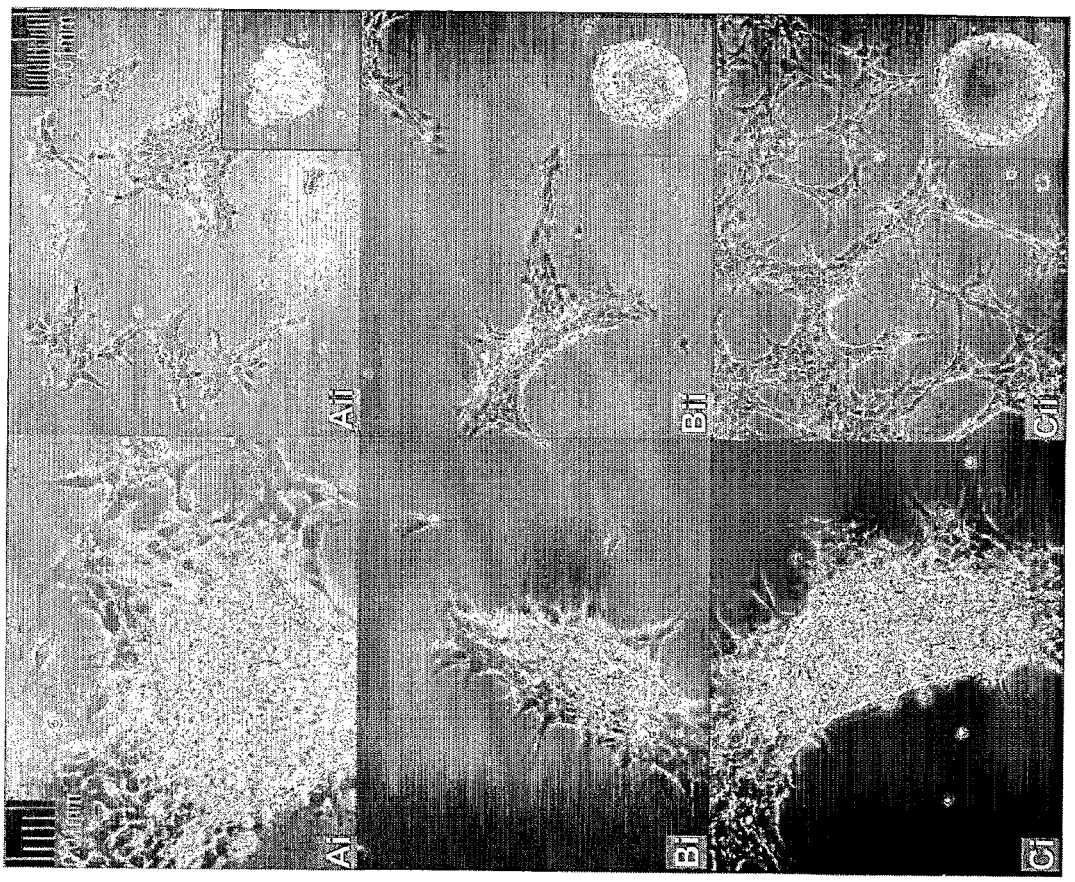
FIG. 3. HES-NPCs and brain-NPCs have indistinguishable morphology in cultures. Bright field images of hES cell-derived and human brain-derived NPCs growing for two weeks in the Expansion Medium (see Materials and Methods in the Examples). Both H9 (A) and H14 (B) hES cell-derived NPCs as well as adult brain-derived NPCs (C) form clusters (i) and lattice-type cultures (ii). At higher densities all cell types may pinch off as floating spheres (inserts).

Molecular characterization of hES-NPCs. With the increasing cell density, hES-NPC's grow as lattices and often form local aggregates or pinch off as floating spheres (FIG. 3). We have noticed that this behavior is common to NPCs derived from both hES cell-derived NPCs as well as human fetal or post mortem brain-derived NPCs. Human NPCs from both sources can be grown as floating spheres, clusters, or monolayers depending on cell density, plastic coating, and medium composition (FIG. 3). Similar behavior was observed for NPCs derived from two different hES cell lines H9 and H14. Although the underlying signaling that determines this behaviors is unclear, we have noticed that interconversion between these cell culture modalities depends on cell density, plate coating and the frequency of medium replacement. Regardless of these morphological variations, molecular characterization demonstrated that hES-NPCs are uniformly positive/negative in respect to molecular markers that distinguish neural precursors from both hESCs and more committed neural lineages.

Figure 4:
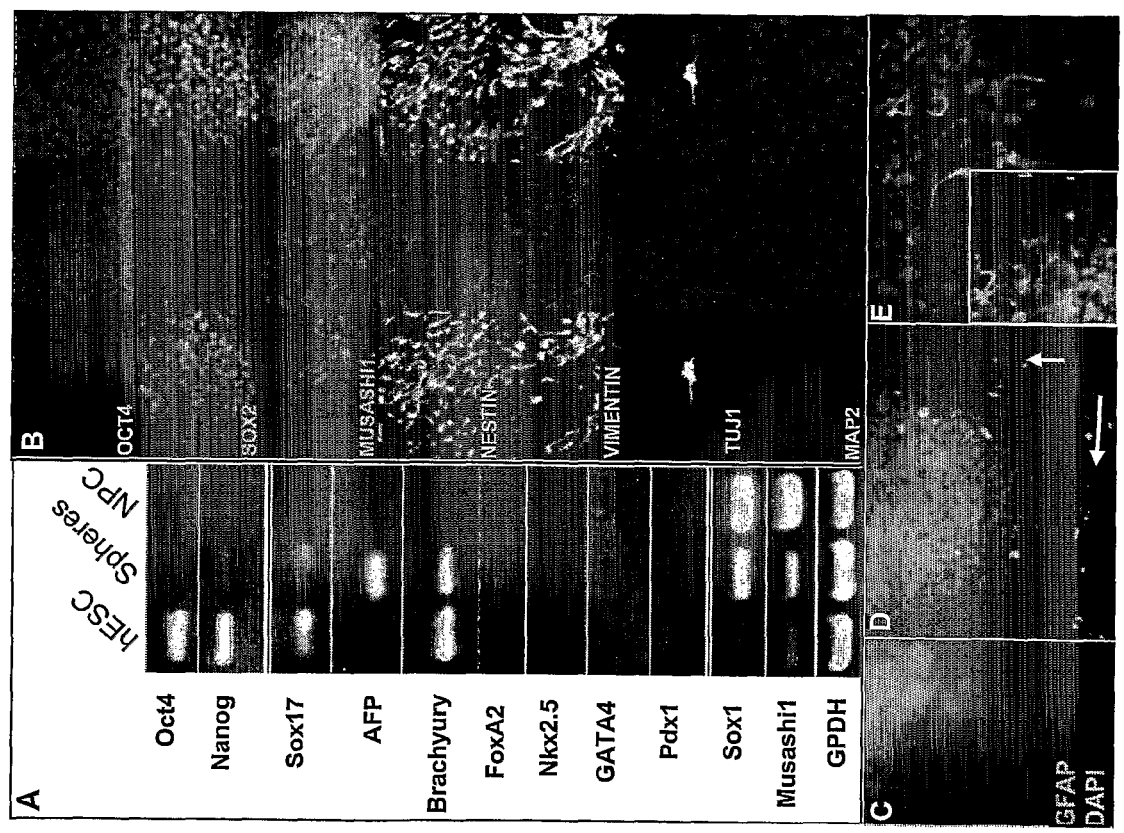
FIG. 4. hES-NPCs express homogenous array of pro-neural markers. (A) the absence of markers characteristic for undifferentiated hESC as well as mesoderm and endoderm was confirmed by RT-PCR; ES cells (0 days), spheres in suspension (6 days of hES differentiation), NPC, neural precursor cells (10 days of hES differentiation). Note the transient upregulation of primitive endodermal markers AFP and Foxo2a (HNF3β) in spheres in suspension. Only neuroectodermal markers Sox1 and Musashi1 are upregulated in hES-NPCs. (B). Immunohistochemistry for developmental markers, left to right columns: fluorescent antibody|DAPI (nuclei) |overlay. Staining for nuclear Oct4, a marker for undifferentiated human ES cells (absent); pronural markers like nuclear Sox2 (uniformly present), cytoplasmic Musashi1 (uniformly present), filamentous Nestin and Vimentin (uniformly present), terminally differentiated neural markers like cytoplasmic TuJ1 (absent, an example of very rare, under 0.1%, positive cell is captured), MAP2 (absent). (C) filamentous GFAP is absent in newly derived NPCs, including identifiable rosettes; (D) some of the cells radiating out of the clusters express GFAP at this stage (arrows in D); (E) in the next passage all NPCs, including the clusters (inset in E) express GFAP.

To identify the presence or the absence of known neural precursor or differentiated cell markers in hES-NPC cultures we have used immunochemistry and RT-PCR respectively (FIG. 4). We found that while uniformly positive for Sox1, Sox2, Musashi1 and Nestin, hES-NPCs were uniformly negative for Oct4, GFAP, MAP2 and O1 markers. The Tuj1-positive young neurons were extremely rare (FIG. 4B). The RT-PCR analysis confirmed the absence the transcripts for Oct4 and Nanog, markers of pluripotent ES cells, GATA-1, a marker of primitive and definitive hematopoiesis, GATA-4, a marker for pharyngeal endoderm and cardiac derivatives, Nkx2.5, a marker of cardiac mesoderm, and PDX-1, a pancreatic marker. We have detected the transcripts for Brachyury/T, Sox 17 and alpha-fetoprotein (AFP) in the spheres growing for 4-6 days in suspension medium (FIG. 4B). These markers, however, were not detected in the hES-NPCs after 4 days of further propagation in the hNPCs expansion medium (FIG. 4A). Remarkably, freshly generated hES-NPCs were negative for GFAP marker (FIG. 4C), however, upon passaging the cells emigrating from the clusters and then all cells in the cultures acquired GFAP marker (FIGS. 4D, F). This is clearly different in the case of brain-derived NPCs, which are uniformly GFAP-positive even at early passages (Palmer et al., *Nature* 411: 42-3, 2001; Schwartz et al., *J Neurosci Res* 74: 838-51, 2003).

Expression analysis of the developmental path from human ES cells to neural precursors. Because of both the beginning (hESCs) and the endpoint (hES-NPCS) populations in our procedure are homogenous with respect to molecular markers used in this study; we were able, for the first time, to investigate the gene expression profile during in vitro transition of human ES cells to neuroepithelium-like cells. Critical differences between human and mouse ES cells (Daheron et al., *Stem Cells* 22: 770-8, 2004; Ginis et al., *Dev Biol* 269: 360-80, 2004; Humphrey et al., *Stem Cells* 22: 522-30, 2004) prompted us to compare neurepithlium transition in human system to that recently published for mouse ES cells (Aiba et al, ePub ahead of print, *Stem Cells* 2005). Contrary to the mouse ES cells to neuroepithelium transition (Aiba et al., 2005) we have not detected the activation of the FGF5 gene, a hallmark of the primitive ectoderm formation (Rathjen et al., *J Cell Sci* 112(5): 601-12, 1999; Rathjen et al., *Reprod Fertil Dev* 13: 15-22, 2001). Similar to mouse differentiation a number of developmentally regulated Hox family genes were found to be upregulated during hESCs to NPCs transition. Some of the detected genes were identical, whereas other were different. Some discrepancies, however, may be due to the differences in the microarray platforms used.

Figure 5:
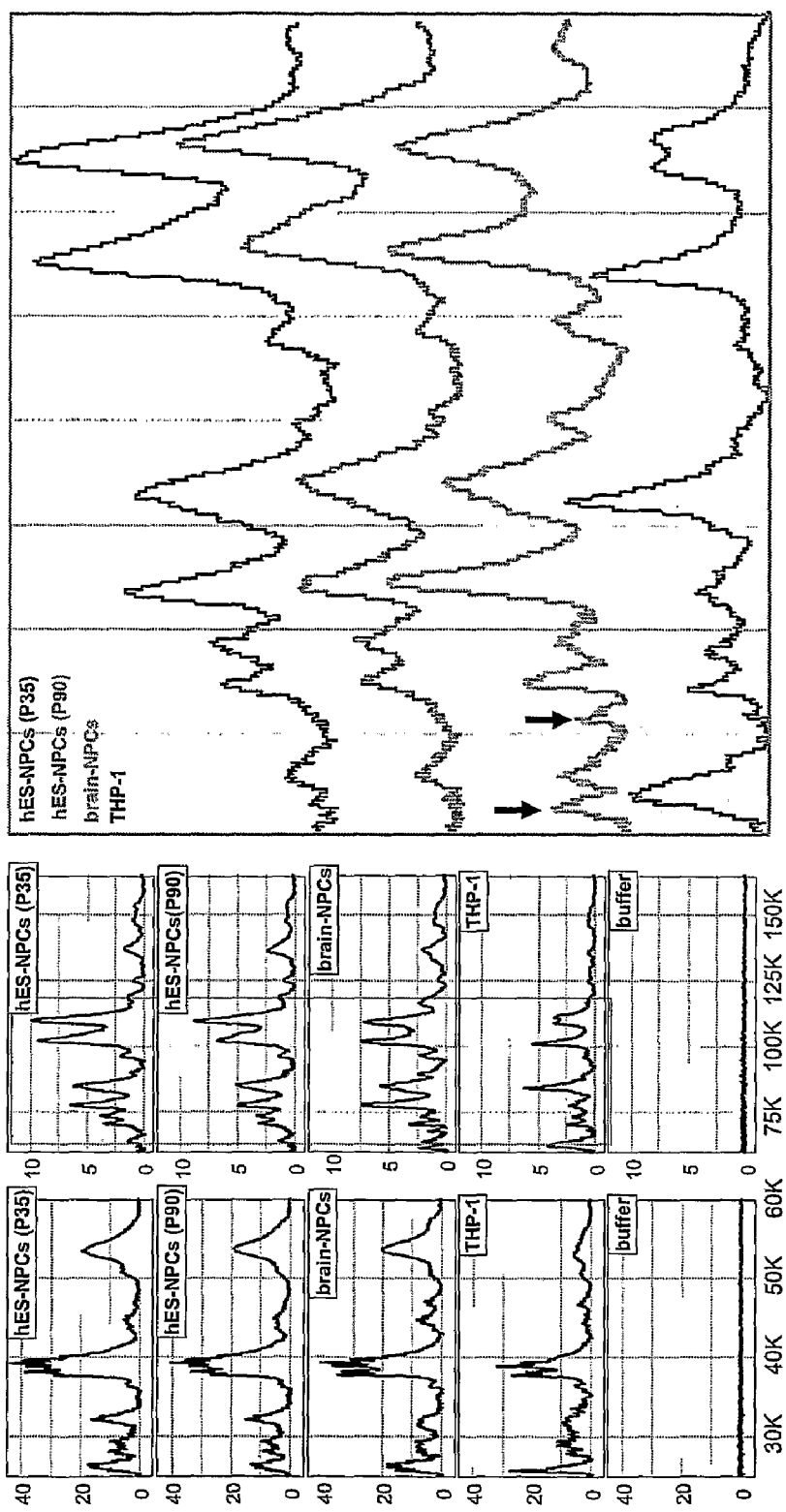
FIG. 5. Proteome profiling of hES-NPCs and brain-NPCs. Surface-enhanced laser desorption ionization mass spectrometry (SELDI-MS) was used for the whole-cell proteome profiling. Cell lysates from hES-NPCs (derived from hESCs (H9), which have been propagated for 35 passages or after 90 passages), brain derived NPCs (15 passages) and human acute monocytic leukemia cell line (THP1) were compared using weak cation-exchanger proteinchip (WCX2). Two left panels represent cellular proteome profile between 30-60 and 75-150 kDa. Right panel is a blowup of the squared area in the second panel. The arrows indicate protein clusters that are differentially expressed between the hES-NPCs and the brain-hNPCs. Note virtually indistinguishable profiles of 35 and 90 passages hESC-derived NPCs, the overall close resemblance of brain-derived NPCs and hES-NPCs profiles and a very distant profile of a human leukemia cell line.

Reproducible proteome signature of hES-NPCs derivations. The reproducibility and robustness of differentiation procedure is critical if we were seriously considering clinical applications. It would be logical to control these parameters quantitatively and on the whole-cell level. We have performed comparative proteome analysis of two independent hES-NPCs derivations from hES cell line (H9). First hES-NPCs were derived from hESCs at passage 35. The additional 55 passages roughly correspond $10^{15}$ fold of cell amplification. We have used two controls: brain-derived NPCs (kind gift of Phil Schwartz, Children's Hospital of Orange County, California) and human acute monocytic leukemia cell line THP-1 (FIG. 5). We have employed SELDI-MS technology (Ciphergen), which combines an adjustable selective adsorption onto a pretreated chip surface based on the physical-chemical properties of a given protein with linear TOF mass spectrometry for the determination of the molecular weight of the adsorbed molecule (Ciphergen Biosystems). Although the exact nature of proteins representing each point of the proteome profile is not known, this technology allows rapid and efficient comparison of the proteome signature i.e. relative amounts and profile shapes (e.g. peaks and valleys) of different cellular preparations. Indeed, the presence and the ratio of protein signals constitute the proteome "signature" of a given cell preparation, which can then be easily compared with the signature from another samples. We have used weak cation-exchanger protein chip (WCX2) recommended for the pilot analysis of complex whole-cell protein mixtures. We have found that the pattern of protein expression in the range of 30-150K is virtually identical for two hES-NPCs cultures (FIG. 5; two upperblue traces). While the proteome profiles of the brain-NPCs cultures clearly shares over-all similarity with the profiles of hES-NPCs (FIG. 5 green traces), differences can be easily discerned (arrows). Although we do not know the nature of these peaks, their presence signals some differences between brain-derived NPCs and hES-NPCs. Clearly, these differences are not presence between two different derivations of hES-NPCs. In contrast, the proteome pattern of the human acute monocytic leukemia THP-1 cell line shows major differences from both NPCs preparations (FIG. 4 black traces; traces appear in the order as listed in the figure; e.g., the THP-1 label is listed fourth; the corresponding THP-1 tracing is the fourth tracing beginning counting from the top of the figure). We interpret these results as a demonstration of robust and reproducible generation of homogeneous hES-NPCs after a large-scale expansion of human ES cells. The results also suggest that the proteomes of hES cell-derived NPCs and brain-derived NPCs are rather similar to each other, and differ drastically from the immortalized human leukemic cells THP-1.

Figure 6:
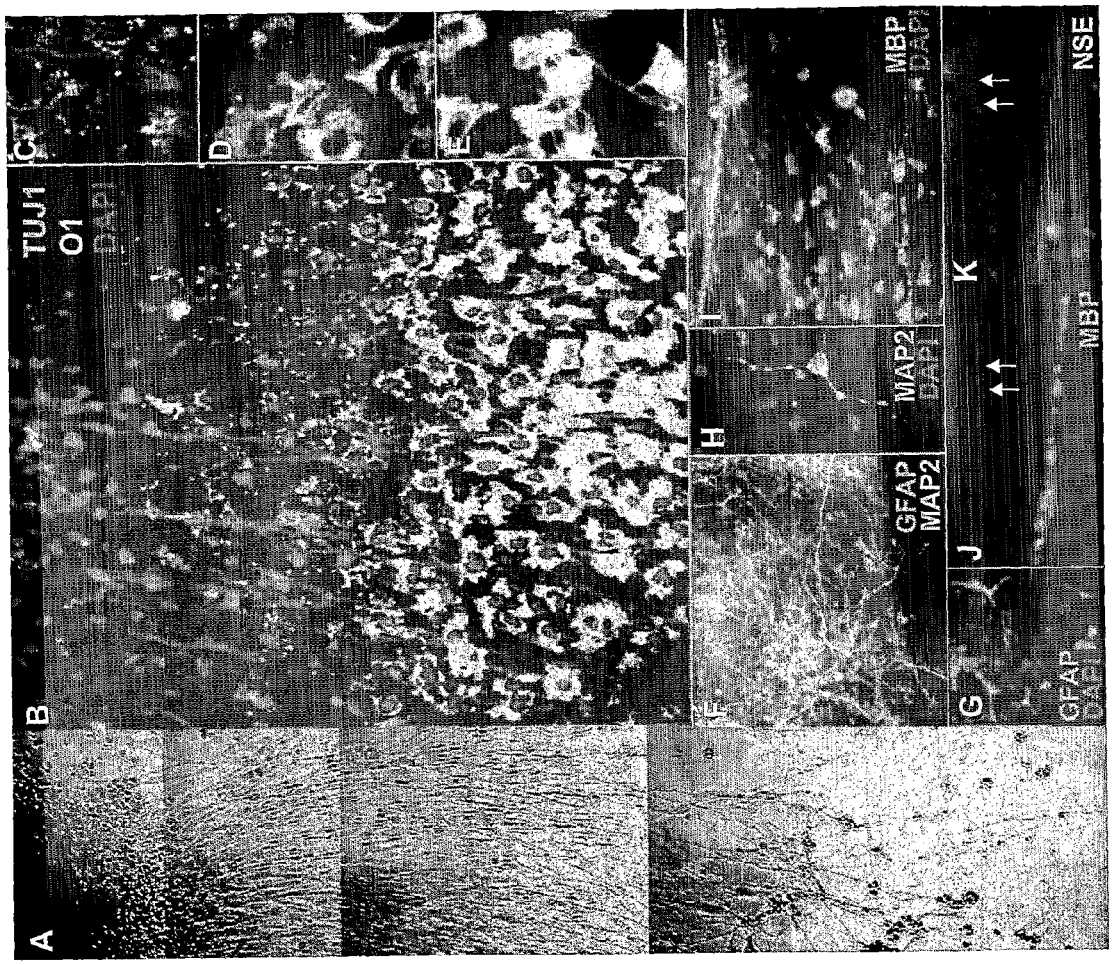
FIG. 6. Differentiation of hES-hNPC results in abundant neurons and functional oligodendrocytes capable of in vitro myelination of neuronal processes. A bright field and B immunostaining of differentiating hES-NPCs colony with radiating Tuj1-positive neurons (red) and O1-poitive maturing oligodendrocytes (green). Note the increase O1 intensity towards the periphery of the colony suggesting the maturation process (C-E). All types of neural cells were represented in each differentiating colonies as illustrated by MAP2, GFAP and O1 staining (B-H). The O1-positive oligodendrocytes express Myelin Basic Protein, (MBP) already at 2 weeks of differentiation (I) and are capable of in vitro myelination of neural processes positive for Neuron Specific Enolase (NSE) (J, K). Cell nuclei are counterstained with DAPI (B-K).

In vitro differentiation of hES-NPCs. Cultures of homogeneous hES-NPCs can be efficiently differentiated into large numbers of TuJ1-positive neurons and O1-positive oligodendrocytes (FIG. 6) upon culture in differentiation medium (DMEM: F12+B27) containing 1% horse serum on ornithin plus laminin-coated plates. Each experiment resulted in all three major neural subtypes originated from the individual: neurons, oligodendrocytes and astrocytes (FIG. 6 B-H). We have observed massive outgrowth from hES-NPC clusters of TuJ1-positive young neurons and O-1 positive oligodendrocytes (FIG. 6 B-H). Interestingly, the O-1 immunostaining was stronger distally from the hES-NPC cluster, suggesting that differentiation and oligodendrocyte maturation occurred during emigration (FIG. 6 B-E). After two weeks of differentiation we have detected multiple processes that stained double-positive for Neuron Specific Enolase (NSE) and Myelin Basic Protein (MBP), the latter was localized to the periphery of the processes. (FIG. 6 I-K). These results suggest that hES cell-derived oligodendrocytes were capable of in vitro myelination of neurons that being generated in the same cultures.

While performing parallel in vitro differentiation of hES cell-derived NPCs and human brain-derived NPCs, we have noticed several differences in regard to the kinetics of the appearance of various differentiated cells. For instance, hES-NPCs require up to 6-10 days producing TuJ1-positive young neurons, while brain-hNPCs will generate Tuj1-positive cells within 3-4 days. This observation is consistent with hESCs-NPCs and brain-NPCs marker analysis above, suggesting that hES-NPCs might represent more immature and less committed neural precursors compared to brain-derived hNPCs.

Figure 7:
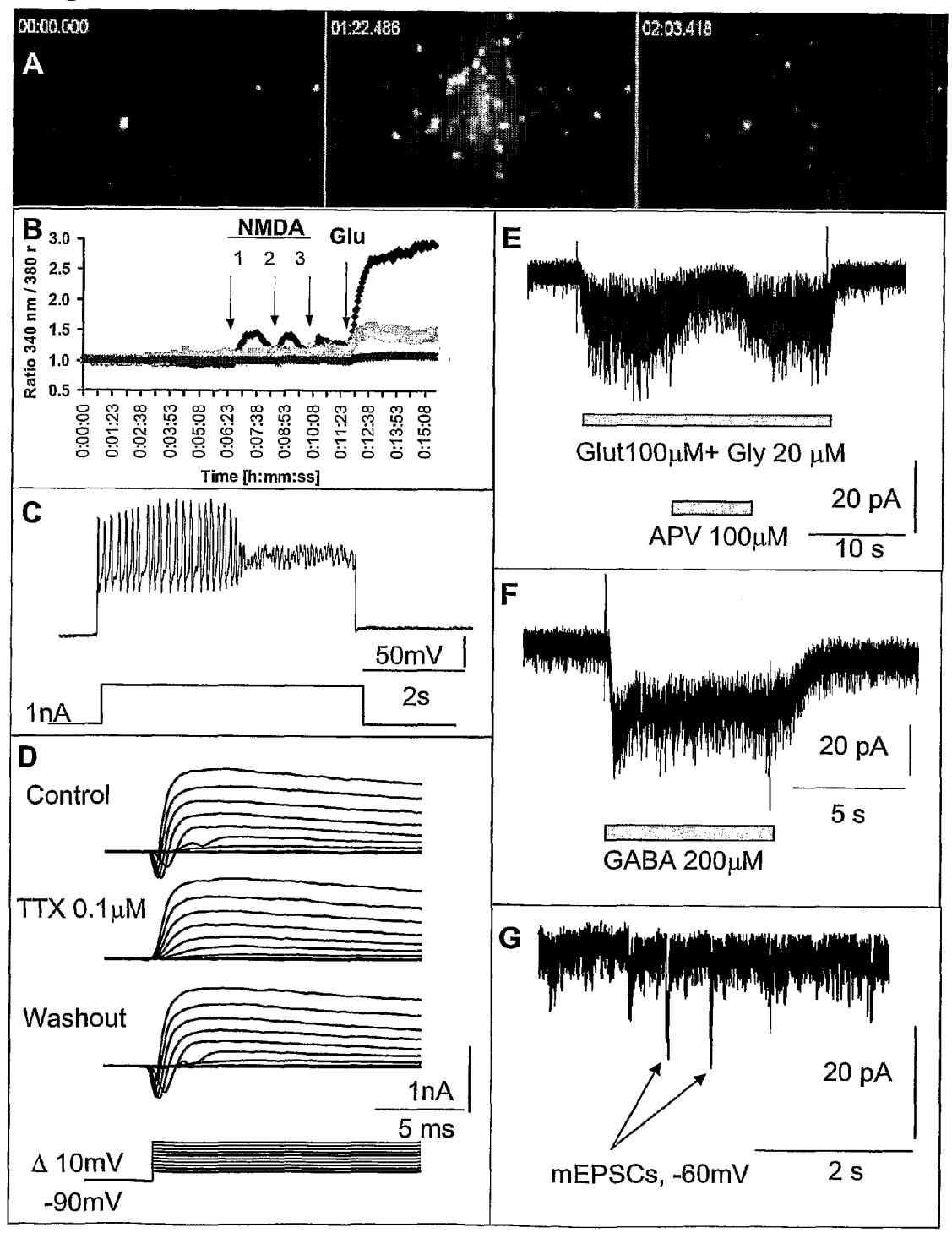
FIG. 7. Characterization of differentiated hES-NPCs as neurons using physiological criteria. NMDA/glutamate induced increases in [Ca2+] in numerous cells derived from hES-NPCs after 2-4 weeks in cultures. (A) Images obtained before and during addition of NMDA to cells loaded with the Ca2+-sensing dye fura-2 (10 µM). (B) Fura-2-loaded cCells were exposed to NMDA and glutamate (1 µM or 1 mM, respectively at 37° C.). Changes in calcium are shown relative to baseline conditions. (C) Action potentials, recorded in current-clamp mode, after depolarization from −50 mV to +12 mV. (D) Voltage-gated Na+ currents, recorded after 4 weeks of differentiation. Fast Na+ currents, but not other outward currents, were reversibly blocked by 0.1 µM TTX. Whole-cell recording in voltage-clamp mode; stimulation consisted of 100 ms voltage steps in 10 mV increments from −60 to +30 mV from a holding potential of −60 mV following a 300-ms hyperpolarizing prepulse to −90 mV. (E, F) Ligand-gated currents, recorded under voltage clamp, from differentiated hES cells after 2.5 weeks in culture. Glutamate-evoked currents were partially inhibited by APV. Holding potential −60 mV. (G) Spontaneous mEPSCs, recorded in voltage-clamp mode, after 2 weeks of differentiation. Holding potential −60 mV.

Electrophysiological analysis of neurons derived from hES-NPCs. To address the functional properties of neurons detected by immunostaining, we have performed calcium imaging of multiple fura-2-loaded neurons and patch-clamp recording from individual cells on 4-5 week old cultures of differentiated hES-NPCs. In the Ca2+ imaging experiments differentiated hES-NPCs cultures were exposed to N-methyl-D-aspartate (NMDA) followed by glutamate (Glu) in order to assess the responsiveness of the cells to ligands of glutamate receptors, the major excitatory neurotransmitter receptors on cerebrocortical neurons (FIG. 7A). Robust responses were found in individual cells from several independent cultures (FIG. 7B). These observations indicated the presence of glutamate receptors that are typically found in cerebrocortical neurons, including the NMDA receptor subtype, in about 10% of all cells in the cultures.

To unambiguously document the presence of mature neurons, we investigated the electrophysiological properties of differentiated hES-NPCs. We performed whole-cell recordings with patch electrodes from hES-NPCs that had differentiated for 2-4 weeks. The presence of voltage-gated channels was detected at different times after the plating. By 4 weeks in culture, about 10% of cells fired action potentials, typical of the neuronal response, when depolarized in the current-clamp mode (FIG. 7C). Importantly, under voltage clamp, we observed sodium currents (blocked by tetrodotoxin) with fast time-course and amplitude of several hundreds of picoamps (FIG. 7D). We have also detected potassium channels and calcium channels in these cells (data not shown). In addition to these voltage-gated currents, we demonstrated the presence of ligand-gated channels in these cells. After 2 weeks in culture, approximately 30% of the cells manifest glutamate-evoked currents, which were partially blocked by 100 μM D-(−)-2 amino-5-phosphonovaleric acid (D-APV, a specific antagonist of NMDA-type glutamate receptors). This result indicates the presence of excitatory NMDA type of glutamate receptors, which are found on neurons (FIG. 7E). In 4 of 29 cells recorded at 2.5 weeks in culture, we observed the γ-aminobutyric acid (GABA)-evoked currents, which can be found on neurons destined to become inhibitory in nature (FIG. 7F).

Regarding synaptic activity, which reflects functional interconnectivity and neurotransmission between cells, several cells had miniature excitatory postsynaptic currents (mEPSCs) after differentiating for 3 weeks. This result indicates formation of synaptic connections between differentiated cells in the culture (FIG. 7G). Taken together, our findings suggest that hES-NPCs are capable of giving rise to neural cells with a variety of electrophysiological properties typical for bona fide neurons.

Original hESCs but not hES-NPCs form teratomas in vivo. Human ES cells and hES-NPCs were examined for their ability to form teratomas in the newborn or adult mice. Out of seven examined newborn mice injected with hES-NPCs, none developed discernable neoplasia. Furthermore, we have performed classical teratoma formation assay by injecting both hESCs and hES-NPCs subcutaneously in SCID mice. Whereas hES cell injections resulted in large teratomas (not shown), hES-NPCs did not cause any tumors, consistent with undetectable levels of Oct4 mRNA in these cells.

Figure 8:
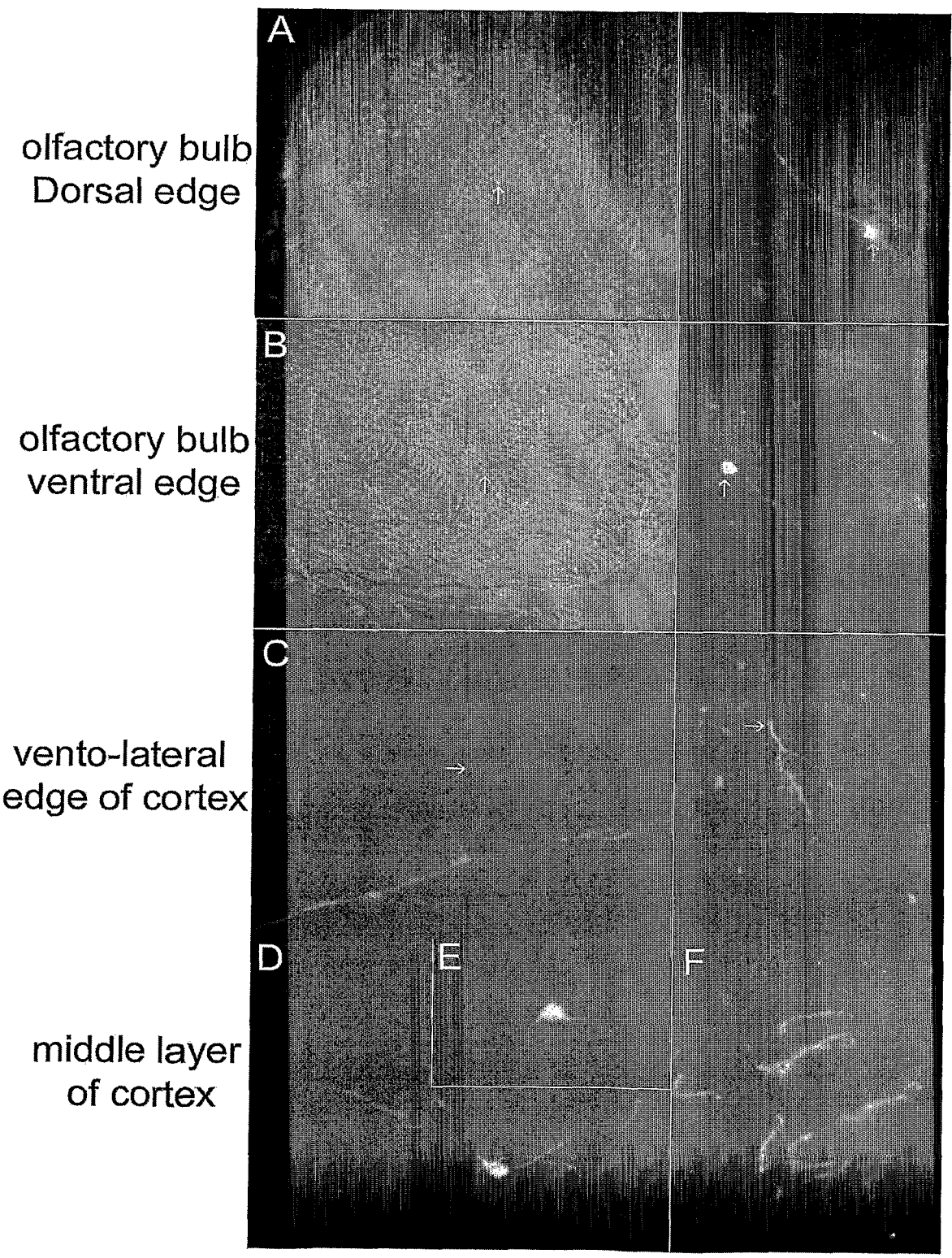
FIG. 8. HES-NPCs can survive migrate and differentiate upon transplantation into mouse brain. The hES-NPCs (passage 6) engineered to express EGFP under the control of ubiquitous hPGK promoter, were injected into the lateral ventricles of the newborn CD1 mice. The mice were sacrificed 10 weeks after injection; the brains were fixed and sectioned. EFGP-positive (epifluorescence) cells were found in multiple locations of the brain (indicated by arrows), suggesting that the injected hES-NPCs have survived and migrated into various brain areas; the outline of transversal brain section is showed in green for visual guidance. (B) Anti-EGFP/HRP staining revealed many bipolar cells with the morphology typical of young neurons scattered over various brain area, including rostral migratory stream and olfactory bulb. Additional sections of the (C) bento-lateral edge of cortex and (D, F) middle layer of cortex show similar migration of the cells (see also insert E for greater detail).

HES-NPCs survive migrate and differentiate upon transplantation into the normal neonatal brain. About $10^5$ hES cell-derived NPCs (passages 2-6) were transduced with lentivirus expressing EGFP under the control of human PGK promoter and transplanted into the lateral ventricles of the newborn CD1 mice. Ten weeks later animals were sacrificed and brains sections were analyzed for the presence of cells expressing EGFP marker. Analysis of EGFP epifluorescence and immunostaining with EGFP-specific antibody revealed numerous EGFP positive cells, often found in large clusters radiating towards the periphery. We have found a wide distribution of human cells, including the olfactory bulb, cortex, striatum and corpus collosum, suggesting rather high migratory potential of injected hES-NPCs (FIG. 8A). Many bipolar cells with elongated processes, characteristic of young migrating neurons were found in olfactory bulb and rostral migratory stream (FIG. 8B). Additional distribution of cells is seen in FIGS. 8C, D and F (see also insert FIG. 8E). These results demonstrate that hES-NPCs can survive, migrate and differentiate upon transplantation into the neonatal brain.

Figure 10:
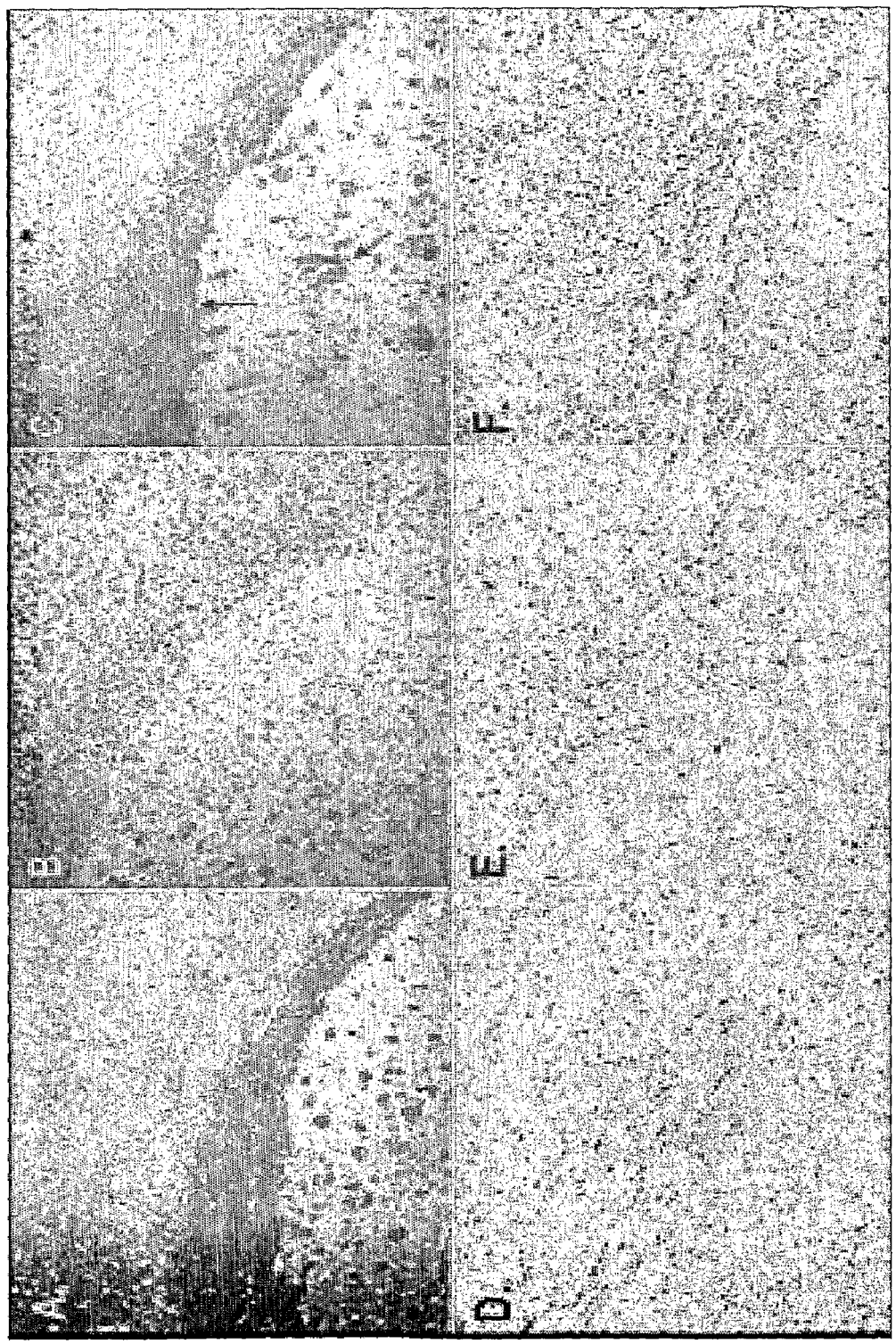
FIG. 10. (A) Control normal section of Corpus Callosum. (B) Brain sections 4 weeks after initiation of Cuprizone treatment injected with Saline at 2 weeks (C) A single injections of 5×105 human ES cell-derived neural precursor cells engineered to express DsRed fluorescent protein; myelin is stained in blue, or dark spots in the figure (Vectastain immunohistochemistry kits with diaminobenzidine as the chromagen) D, E, F adjacent sections corresponding to the upper sections stained with anti-DsRed antibodies (dark staining in F).

HES-NPCs prevent Cuprizon-induced demyelination of corpus callosum after systemic administration. Dietary consumption of cuprizone, a copper chelator, produces significant demyelination in C57B1/6 mice that is most notable in the corpus callosum (Matsushima and Morell, 2001). Two weeks following the initiation of the cuprizone diet mice were injected intravenously into the tail vein with $5 \times 10^5$ hES-NPCs, following additional two weeks of cuprizone administration. At the four week time point (maximum of cuprizone-induced demyelination) we have analyzed the degree of myelination in control (saline) and hES-NPCs injected mice (FIG. 10). We have found that demyelination of corpus callosum was effectively prevented in the experimental brains but not in the control brains. Immunohistochemical detection of dsRed suggested the presence of human cells in and around the myelinated areas of corpus callosum and the neighboring axonal tracts.

Discussion

Despite of several published reports of human ES cells differentiation into neural precursors, none provides the continuous culturing procedure resulting in pure population of NPCs. In all previous cases mechanical separation, extended cultures (over 2 months) or antibody-based enrichment were required to obtain relatively pure cultures of hES-NPCs (Carpenter et al., *Exp Neurol* 172: 383-97, 2001; Zhang et al., *Nat Biotechnol* 19: 1129-33, 2001; Tabar et al., *Nat Biotechnol* 23: 601-6, 2005). The advantages of rapid (~12 days), near-quantitative conversion of hESCs into neural precursors are three folds. First—our procedure uses fully define medium, which does contain serum or any pleiotropic factors such as retinoic acid (RA) that might uncontrollably affect the cell fate (e.g. transformation to posterior CNS neurons (Li et al., *Nat Biotechnol* 23: 215-21, 2005)). The start and the end point population are homogenous with respect to the molecular markers currently used to define hESCs and neural precursors. Thus, this is the first controlled system allowing the modeling and dissection of the molecular pathways of neuroepithelium differentiation in human ES cells. Second—the extensive in vitro expansion of mouse neural precursors renders those non-responsive to environmental signals and result in loss of their positional identity (Santa-Olalla et al., *Eur J Neurosci* 18: 1073-84, 2003). It is quite possible that extensive expansion of hES-NPCs will result in genetic and epigenetic changes resulting in progressive loss of the specific neural fates upon terminal differentiation. For instance, niche-independent extensive expansion of ES cell-derived neural stem cells might account for the lack of appreciable amounts of oligodendrocytes generated upon differentiation differentiation (Conti et al., *PLoS Biol* 3: e283, 2005). Our preliminary data indicate similar trait in the advanced passages of hES-NPCs. Third—this procedure is technically straightforward and eliminates the differential enzymatic digestion and other cell selection steps. The desired cell population can be generated from any human ES cells line (e.g. clinically relevant GMP-derived hESCs) within days by a fully and easily controllable protocol. Finally, compared to all previous approaches this is a much simpler technique, which can be realistically amenable for clinical applications outside of the research laboratory environment.

Critical steps for the efficient differentiation of hES cell into NPCs. We found that starting with 4 day hESC colonies was important to produce well-growing spheroid bodies in suspension medium. This is likely because of minimizing the amounts of partially differentiated human cells and initial enrichment for highly proliferative uncommitted hESCs.

Crucial to our protocol were the extensive PBS washes, which serve to eliminate partially differentiated hESCs, residual MEFs and debris. It has been observed that spontaneous differentiation of hESCs always occurs, even in the best conditions. These cells are likely to be the source of non-neuronal cell types that arise in the cultures, probably as a consequence of secreted factors or cell-cell interactions among themselves or with pluripotent hESCs. We have been able to derive hES-NPCs after up to 5 passages on matrigel and we found that gentle trituration and multiple washes with PBS were effective at eliminating the residual MEFs and differentiating hESCs, which we believe might have compromised prior attempts at neural differentiation under similar differentiation conditions. Our results suggest that the exposure of pure uncommitted hES cells to serum free medium supplemented with bFGF and EGF is sufficient to convert hES cells into neural precursors. Our findings parallel those that were reported recently for the differentiation of mESCs into neuronal lineages (Bibel et al., *Nat Neurosci* 7: 1003-9, 2004). However, contrary to the conditions described by Bibel et al., for generation of homogeneous mESC-derived NPCs, our protocol uses a defined medium. Defined conditions should lead to a better understanding of the growth factor requirements and signaling cascades that control directed neural differentiation of hESCs.

Interestingly, we have observed a healthier morphology of spheroid bodies and subsequent uniform formation of rosettes upon addition of NAC to the suspension medium. NAC is a precursor of the intracellular glutathione and a known (van Zandwijk, *J Cell Biochem* 22: 24-32, 1995; Deneke, *Curr Top Cell Regul* 36: 151-80, 2000). NAC has been previously used influence the intracellular redox state, which appears to be a critical modulator of differentiation fate in oligodendrocyte-type-2 astrocyte (O-2A) precursor cells cells (Smith et al., *Proc Natl Acad Sci USA* 97: 10032-7, 2000). It has been further proposed that intra-cellular redox conditions may be a general regulator, influencing the balance between self-renewal and differentiation in dividing precursor cells (Noble et al., *Ann N Y Acad Sci* 991: 251-71, 2003). Along these lines, the addition of NAC might promote the maintenance of neural precursors and slow down the spontaneous differentiation.

Functional characterization of hES-NPCs. We have demonstrated that hES-NPCs described in this paper can give rise to functional differentiated cells both in vitro and in vivo. Large spectrum of neuronal activities was recorded in vitro suggesting that hES-NPCs are capable of producing broad spectrum of functional CNS neurons. On the other hands oligodendrocytes generated were capable of producing myelin basic protein, which was colocolized with neuronal processes, suggesting their in vitro myelination. Upon transplantation into the lateral ventricles of the newborn nice hES-NPCs were found both as single cell and as clusters with clear neuronal morphologies. Finally, we have demonstrated the rescue of demyelination in corpus callosum of the Cuprizone-treated mice. Treatment with cuprizone for a period of four consecutive weeks results in predictable and consistent demyelination of the corpus callosum. Cuprizone-induced demyelination is associated with significant microgliosis and macrophage recruitment (Bakker and Ludwin, *J Neurol Sci* 78: 125-37, 1987; Hiremath et al., *J Neuroimmunol* 92: 38-49, 1998; McMahon et al., *J Neuroimmunol* 130: 32-45, 2002), but does has minimal T-cell responses (Matsushima and Morell, *Brain Pathol* 11: 107-16, 2001). The consistent and predictable nature of the site of myelin injury in this model results in easily quantifiable change in corpus callosum myelination. These changes might result from the de-novo myelination by oligodendrocytes derived from hES-NPCs, however, prevention of terminal demyelination by immunomodulatory mechanisms (Pluchino et al., *Nature* 436: 266-71, 2005), can be a viable alternative explanation.

Brain-derived hNPCs vs hES cell-derived NPCs. Due to the lack of specific markers prospective isolation of human NPCs is challenging and commonly used brain-derived NPC cultures are quite heterogeneous, containing cells expressing the markers of differentiated neural lineages (Palmer et al., *Nature* 411: 42-3, 2001; Schwartz et al., *J Neurosci Res* 74: 838-51, 2003). Despite very similar cellular morphologies, hES cell-derived NPCs do not express the markers of differentiated cells but stain rather homogeneously for Sox1, Sox2, Musashi1 and Nestin. Thus, brain and hESC-derived NPCs strategies for transplantation (FIG. 9) have contrasting challenges and opportunities.

Human tissues are available in limited amounts and are intrinsically heterogeneous. In addition, the collection and use of the fetal material poses serious ethical and logistical problems. This is the major obstacle for a wide use of primary human cells for therapy or even research purposes. For example, in the case of Parkinson's disease, up to 7 human fetuses were used to treat a single patient (Kordower et al., *N Engl J Med* 332: 1118-24, 1995). One proposed possibility is to generate large cell numbers from limited primary brain tissue by oncogene-mediated immortalization immortalization (Cepko, *Trends Neurosci* 11: 6-8, 1988), (Lendahl and McKay, *Trends Neurosci* 13: 132-7, 1990; Snyder, *Proc. Assoc. Am. Physicians* 107: 195-204, 1995). However, the frequently unstable phenotype of these cells and the concern of grafting cells with potential oncogenic capacity has dampened the initial enthusiasm for this strategy. Another possibility is the expansion of undifferentiated NPCs in serum-free medium with defined growth factors. There is growing evidence, however, that extended expansion of NPCs in vitro alters their characteristics. The growth factor dependence (bFGF vs EGF) and the expression of particular transcription factors (such as Emx2, En2, Krox20, Hox genes, Pax6,7, Dbx1 and Nkx2.1) is apparently not preserved during long-term culture of NPC populations derived from different areas of the mouse CNS (Santa-Olalla et al., *Eur J Neurosci* 18: 1073-84, 2003). The neurospheres becomes non-responsive to environmental signals from early passages in vitro as the positional identity of neurospheres does not change when expanded in the presence of patterning such as Shh, FGF8 and RA (Santa-Olalla et al., *Eur J Neurosci* 18: 1073-84, 2003). Importantly, this phenomenon is not observed in NPCs generated in vitro from mouse embryonic stem cells (Lee et al., *Nat Biotechnol* 18: 675-9, 2000; Wichterle et al., *Cell* 110: 385, 2002).

Our preliminary experiments demonstrate that homogenous hES cell-derived NPCs can survive, migrate, and differentiate upon transplantation into the lateral ventricles of the new born mice. This is consistent with prior reports that human ES cell-derived NPCs transplanted into chick (Goldstein et al., *Dev Dyn* 225: 80-6, 2002), neonate mice (Zhang et al., *Nat Biotechnol* 19: 1129-33, 2001) and rats (Ben-Hur et al., *Stem Cells* 22: 1246-55, 2004) show cell survival, migration and differentiation into neurons astrocytes and oligodendrocytes. HESC-derived NPCs offer advantages over amplified human brain-derived neural precursors. Despite good survival amplified human brain derived NPCs transplanted into a rat model of Parkinson's disease exhibited low incidence of differentiation into neurons (5%), migration towards lesions, or evidence of proliferation ($\leq 1.5\%$). (Cadwell and Joyce, *PCR Methods* 2: 28-33, 1992). Consequently, no cells were seen within the lesion cavities and no signs of improvement were detected. This is in contrast to a number of reports where NPCs migration towards brain lesions was considered to be a hallmark of neural stem/precursor cells (Park et al., *Gene Ther* 9: 613-24, 2002). Thus, we are currently investigating the potential of NPCs derived from hESCs by our protocol to repair the damaged brain in the rodent models of stroke and impaired myelination.

In summary, we have demonstrated the near-quantitative conversion of human ES cell into NPCs. We believe that the generation of homogenous cultures of transplantable human ES cell-derived NPCs opens new horizons for evaluation of applying this regimen to neural regeneration. Ongoing studies will compare the differentiation and regenerative potential of hESC and human brain-derived NPCs. In addition, the use of formulated medium and defined conditions will aid the characterization of extracellular signals and intracellular cascades that control the generation of neural subtypes, as recently exploited for spinal cord and telencephalic neurons (Li et al., *Nat Biotechnol* 23: 215-21, 2005; Watanabe et al., *Nat Neurosci* 8: 288-96, 2005).

On the other hand, homogeneous hESCs-derived transplantable hNPCs could be the perfect staring point for the define population of neurons using stromal co-cultures (Kawasaki et al., Neuron 28: 31-40, 2000) and the introduction of transcription factors such as Nurr1 (Chung et al., *Eur J Neu-* rosci 16: 1829-38, 2002; Kim et al., *Nature* 418: 50-6, 2002) for motor neurons and dopaminergic neurons. Soluble factors, such as sonic hedgehog, were used to guide the generation of transplantable motor neurons (Wichterle et al., *Cell* 110: 385, 2002). However, even in the best conditions, only a small percent of human ES cell-derived midbrain dopamine neurons are electrophysiological active (Perrier et al., *Proc Natl Acad Sci USA* 101: 12543-8, 2004).

Figure 9:
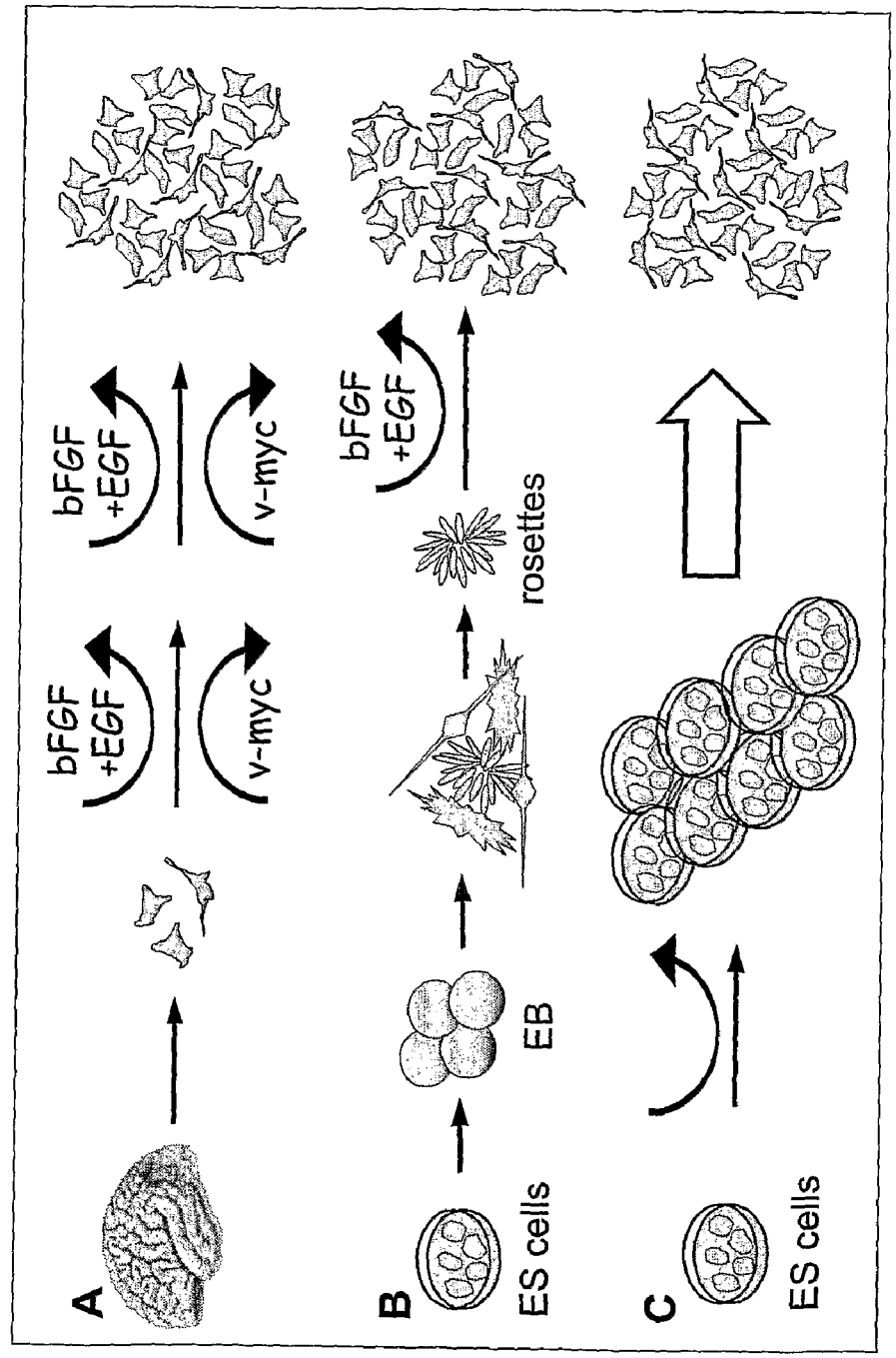
FIG. 9. Three alternative strategies of generating transplantable human neural precursors. (A) The limited amounts of primary highly heterogeneous brain-derived NPCs must be extensively amplified, for instance by immortalization with c-myc or using growth factor combination e.g. bFGF+EGF; certain type of precursor cells may be lost or selected by growth requirements (B) human ES cells has been shown to generate NPCs through a variety of differentiation protocols, which invariable include formation of Embryoid Bodies (EB), adhesion cultures where scattered rosettes can be isolated through differential enzymatic digestion, and extensive expansion using combination of mitogenes; (C) alternatively, in our approach hESCs are the cells to be expanded and then quantitatively converted into NPCs. The latter rapid homogeneous conversion maximally preserves the wide range of the differentiation fates and can greatly facilitate the dissection of the mechanism controlling ES cell differentiation.

We have developed a culture system using a defined medium that allows hESCs to generate a population of neural precursors, homogenous with respect to markers used in our study. capable of differentiation into neurons, oligodendrocytes and astrocytes. We have demonstrated that hES-NPCs obtained in these studies are homogenously committed to the neural fates and are capable of differentiation into "generic" TuJ1, MAP2, and NSE-positive neurons, O1-positive oligodendrocytes and astrocytes. Moreover, the neurons that were obtained after 2-4 weeks differentiation of hES-NPCs exhibited electrophysiological properties characteristic of bona fide human neurons. In addition, the neuronal processes were myelinated in vitro, presumably by hES-NPCs-derived oligodendrocytes, abundantly present in the same cultures. In contrast to all previous studies where a limited numbers of original NPCs were obtained from human brain tissues or HESC and then extensively amplified in vitro using oncogene immortalization or mitogenes, our strategy relies solely on the in vitro expansion of hESC, whereas hES-NPCs are spared of expansion thus preserving their widest differentiation potential (FIG. 9).

REFERENCES

Aiba, K., Sharov, A. A., Carter, M. G., Foroni, C., Vescovi, A. L., and Ko, M. S. (2005). Defining a developmental path to neural fate by global expression profiling of mouse embryonic stem cells and adult neural stem/progenitor cells. Stem Cells.

Aubert, J., Stavridis, M. P., Tweedie, S., O'Reilly, M., Vierlinger, K., Li, M., Ghazal, P., Pratt, T., Mason, J. O., Roy, D., and Smith, A. (2003). Screening for mammalian neural genes via fluorescence-activated cell sorter purification of neural precursors from Sox1-gfp knock-in mice. Proc Natl Acad Sci USA 100 Suppl 1, 11836-11841.

Bakker, D. A., and Ludwin, S. K. (1987). Blood-brain barrier permeability during Cuprizone-induced demyelination. Implications for the pathogenesis of immune-mediated demyelinating diseases. J Neurol Sci 78, 125-137.

Ben-Hur, T., Idelson, M., Khaner, H., Pera, M., Reinhartz, E., Itzik, A., and Reubinoff, B. E. (2004). Transplantation of human embryonic stem cell-derived neural progenitors improves behavioral deficit in Parkinsonian rats. Stem Cells 22, 1246-1255.

Bibel, M., Richter, J., Schrenk, K., Tucker, K. L., Staiger, V., Korte, M., Goetz, M., and Barde, Y. A. (2004). Differentiation of mouse embryonic stem cells into a defined neuronal lineage. Nat Neurosci 7, 1003-1009.

Cadwell, R. C., and Joyce, G. F. (1992). Randomization of genes by PCR mutagenesis. PCR Methods Appl 2, 28-33.

Carpenter, M. K., Inokuma, M. S., Denham, J., Mujtaba, T., Chiu, C. P., and Rao, M. S. (2001). Enrichment of neurons and neural precursors from human embryonic stem cells. Exp Neurol 172, 383-397.

Cepko, C. (1988). Immortalization of neural cells via oncogene transduction. Trends Neurosci 11, 6-8.

Chung, S., Sonntag, K. C., Andersson, T., Bjorklund, L. M., Park, J. J., Kim, D. W., Kang, U. J., Isacson, O., and Kim, K. S. (2002). Genetic engineering of mouse embryonic stem cells by Nurr1 enhances differentiation and maturation into dopaminergic neurons. Eur J Neurosci 16, 1829-1838.

Conti, L., Pollard, S. M., Gorba, T., Reitano, E., Toselli, M., Biella, G., Sun, Y., Sanzone, S., Ying, Q. L., Cattaneo, E., and Smith, A. (2005). Niche-independent symmetrical self-renewal of a mammalian tissue stem cell. PLoS Biol 3, e283.

D'Amour, K. A., Agulnick, A. D., Eliazer, S., Kelly, O. G., Kroon, E., and Baetge, E. E. (2005). Efficient differentiation of human embryonic stem cells to definitive endoderm. Nat Biotechnol 23, 1534-1541.

Daheron, L., Opitz, S. L., Zaehres, H., Lensch, W. M., Andrews, P. W., Itskovitz-Eldor, J., and Daley, G. Q. (2004). LIF/STAT3 signaling fails to maintain self-renewal of hu-man embryonic stem cells. Stem Cells 22, 770-778.

Deneke, S. M. (2000). Thiol-based antioxidants. Curr Top Cell Regul 36, 151-180.

Flax, J. D., Aurora, S., Yang, C., Simonin, C., Wills, A. M., Billinghurst, L. L., Jendoubi, M., Sidman, R. L., Wolfe, J. H., Kim, S. U., and Snyder, E. Y. (1998). Engraftable human neural stem cells respond to developmental cues, replace neurons, and express for-eign genes. Nat Biotechnol 16, 1033-1039.

Ginis, I., Luo, Y., Miura, T., Thies, S., Brandenberger, R., Gerecht-Nir, S., Amit, M., Hoke, A., Carpenter, M. K., Itskovitz-Eldor, J., and Rao, M. S. (2004). Differences between human and mouse embryonic stem cells. Dev Biol 269, 360-380.

Goldstein, R. S., Drukker, M., Reubinoff, B. E., and Benvenisty, N. (2002). Integration and differentiation of human embryonic stem cells transplanted to the chick embryo. Dev Dyn 225, 80-86.

Good, P., Yoda, A., Sakakibara, S., Yamamoto, A., Imai, T., Sawa, H., Ikeuchi, T., Tsuji, S., Satoh, H., and Okano, H. (1998). The human Musashi homolog 1 (MSI1) gene encod-ing the homologue of Musashi/Nrp-1, a neural RNA-binding protein putatively expressed in CNS stem cells and neural progenitor cells. Genomics 52, 382-384.

Hiremath, M. M., Saito, Y., Knapp, G. W., Ting, J. P., Suzuki, K., and Matsushima, G. K. (1998). Microglial/macrophage accumulation during cuprizone-induced demyelination in C57BL/6 mice. J Neuroimmunol 92, 38-49.

Hornstein, E., and Benvenisty, N. (2004). The "brainy side" of human embryonic stem cells. J Neurosci Res 76, 169-173.

Humphrey, R. K., Beattie, G. M., Lopez, A. D., Bucay, N., King, C. C., Firpo, M. T., Rose-John, S., and Hayek, A. (2004). Maintenance of pluripotency in human embryonic stem cells is STAT3 independent. Stem Cells 22, 522-530.

Kawasaki, H., Mizuseki, K., Nishikawa, S., Kaneko, S., Kuwana, Y., Nakanishi, S., Ni-shikawa, S. I., and Sasai, Y. (2000). Induction of midbrain dopaminergic neurons from ES cells by stromal cell-derived inducing activity. Neuron 28, 31-40.

Keyoung, H. M., Roy, N. S., Benraiss, A., Louissaint, A., Jr., Suzuki, A., Hashimoto, M., Rashbaum, W. K., Okano, H., and Goldman, S. A. (2001). High-yield selection and extraction of two promoter-defined phenotypes of neural stem cells from the fetal human brain. Nat Biotechnol 19, 843-850.

Kim, J. H., Auerbach, J. M., Rodriguez-Gomez, J. A., Velasco, I., Gavin, D., Lumelsky, N., Lee, S. H., Nguyen, J., Sanchez-Pernaute, R., Bankiewicz, K., and McKay, R. (2002). Dopamine neurons derived from embryonic stem cells function in an animal model of Parkinson's disease. Nature 418, 50-56.

Kordower, J. H., Freeman, T. B., Snow, B. J., Vingerhoets, F. J., Mufson, E. J., Sanberg, P. R., Hauser, R. A., Smith, D. A., Nauert, G. M., Perl, D. P., and et al. (1995). Neuropathological evidence of graft survival and striatal reinnervation after the transplantation of fetal mesencephalic tissue in a patient with Parkinson's disease. N Engl J Med 332, 1118-1124.

Lee, S. H., Lumelsky, N., Studer, L., Auerbach, J. M., and McKay, R. D. (2000). Efficient generation of midbrain and hindbrain neurons from mouse embryonic stem cells. Nat Biotechnol 18, 675-679.

Lendahl, U., and McKay, R. D. (1990). The use of cell lines in neurobiology. Trends Neurosci 13, 132-137.

Li, X. J., Du, Z. W., Zarnowska, E. D., Pankratz, M., Hansen, L. O., Pearce, R. A., and Zhang, S. C. (2005). Specification of motoneurons from human embryonic stem cells. Nat Biotechnol 23, 215-221.

Lindvall, O., Kokaia, Z., and Martinez-Serrano, A. (2004). Stem cell therapy for human neurodegenerative disorders-how to make it work. Nat Med 10 Suppl, S42-50.

Matsushima, G. K., and Morell, P. (2001). The neurotoxicant, cuprizone, as a model to study demyelination and remyelination in the central nervous system. Brain Pathol 11, 107-116.

McMahon, E. J., Suzuki, K., and Matsushima, G. K. (2002). Peripheral macrophage recruitment in cuprizone-induced CNS demyelination despite an intact blood-brain barrier. J Neuroimmunol 130, 32-45.

Nakano, I., Paucar, A. A., Bajpai, R., Dougherty, J. D., Zewail, A., Kelly, T. K., Kim, K. J., On, J., Groszer, M., Imura, T., et al. (2005). Maternal embryonic leucine zipper kinase (MELK) regulates multipotent neural progenitor proliferation. J Cell Biol 170, 413-427.

Naldini, L., and Verma, I. M. (2000). Lentiviral vectors. Adv Virus Res 55, 599-609.

Noble, M., Smith, J., Power, J., and Mayer-Proschel, M. (2003). Redox state as a central modulator of precursor cell function. Ann N Y Acad Sci 991, 251-271.

Odorico, J. S., Kaufman, D. S., and Thomson, J. A. (2001). Multilineage differentiation from human embryonic stem cell lines. Stem Cells 19, 193-204.

Palmer, T. D., Schwartz, P. H., Taupin, P., Kaspar, B., Stein, S. A., and Gage, F. H. (2001). Cell culture. Progenitor cells from human brain after death. Nature 411, 42-43.

Park, K. I., Ourednik, J., Ourednik, V., Taylor, R. M., Aboody, K. S., Auguste, K. I., Lachyankar, M. B., Redmond, D. E., and Snyder, E. Y. (2002). Global gene and cell replacement strategies via stem cells. Gene Ther 9, 613-624.

Perrier, A. L., Tabar, V., Barberi, T., Rubio, M. E., Bruses, J., Topf, N., Harrison, N. L., and Studer, L. (2004). Derivation of midbrain dopamine neurons from human embryonic stem cells. Proc Natl Acad Sci USA 101, 12543-12548.

Plachta, N., Bibel, M., Tucker, K. L., and Barde, Y. A. (2004). Developmental potential of defined neural progenitors derived from mouse embryonic stem cells. Development 131, 5449-5456.

Pluchino, S., Zanotti, L., Rossi, B., Brambilla, E., Ottoboni, L., Salani, G., Martinello, M., Cattalini, A., Bergami, A., Furlan, R., et al. (2005). Neurosphere-derived multipotent precursors promote neuroprotection by an immunomodulatory mechanism. Nature 436, 266-271.

Rathjen, J., Dunn, S., Bettess, M. D., and Rathjen, P. D. (2001). Lineage specific differentiation of pluripotent cells in vitro: a role for extraembryonic cell types. Reprod Fertil Dev 13, 15-22.

Rathjen, J., Lake, J. A., Bettess, M. D., Washington, J. M., Chapman, G., and Rathjen, P. D. (1999). Formation of a primitive ectoderm like cell population, EPL cells, from ES cells in response to biologically derived factors. J Cell Sci 112 (Pt 5), 601-612.

Reubinoff, B. E., Itsykson, P., Turetsky, T., Pera, M. F., Reinhartz, E., Itzik, A., and Ben-Hur, T. (2001). Neural progenitors from human embryonic stem cells. Nat Biotechnol 19, 1134-1140.

Santa-Olalla, J., Baizabal, J. M., Fregoso, M., del Carmen Cardenas, M., and Covarrubias, L. (2003). The in vivo positional identity gene expression code is not preserved in neural stem cells grown in culture. Eur J Neurosci 18, 1073-1084.

Schwartz, P. H., Bryant, P. J., Fuja, T. J., Su, H., O'Dowd, D. K., and Klassen, H. (2003). Isolation and characterization of neural progenitor cells from post-mortem human cortex. J Neurosci Res 74, 838-851.

Smith, J., Ladi, E., Mayer-Proschel, M., and Noble, M. (2000). Redox state is a central modulator of the balance between self-renewal and differentiation in a dividing glial pre-cursor cell. Proc Natl Acad Sci USA 97, 10032-10037.

Snyder, E. Y. (1995). Immortalized neural stem cells: insights into development; prospects for gene therapy and repair. Proc Assoc Am Physicians 107, 195-204.

Snyder, E. Y., Park, K. I., Flax, J. D., Liu, S., Rosario, C. M., Yandava, B. D., and Aurora, S. (1997). Potential of neural "stem-like" cells for gene therapy and repair of the degenerating central nervous system. Adv Neurol 72, 121-132.

Tabar, V., Panagiotakos, G., Greenberg, E. D., Chan, B. K., Sadelain, M., Gutin, P. H., and Studer, L. (2005). Migration and differentiation of neural precursors derived from human embryonic stem cells in the rat brain. Nat Biotechnol 23, 601-606.

Tamaki, S., Eckert, K., He, D., Sutton, R., Doshe, M., Jain, G., Tushinski, R., Reitsma, M., Harris, B., Tsukamoto, A., et al. (2002). Engraftment of sorted/expanded human central nervous system stem cells from fetal brain. J Neurosci Res 69, 976-986.

Tenneti, L., D'Emilia, D. M., Troy, C. M., and Lipton, S. A. (1998). Role of caspases in N-methyl-D-aspartate-induced apoptosis in cerebrocortical neurons. J Neurochem 71, 946-959.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blas-tocysts. Science 282, 1145-1147.

van Zandwijk, N. (1995). N-acetylcysteine (NAC) and glutathione (GSH): antioxidant and chemopreventive properties, with special reference to lung cancer. J Cell Biochem Suppl 22, 24-32.

Watanabe, K., Kamiya, D., Nishiyama, A., Katayama, T., Nozaki, S., Kawasaki, H., Watanabe, Y., Mizuseki, K., and Sasai, Y. (2005). Directed differentiation of telencephalic precursors from embryonic stem cells. Nat Neurosci 8, 288-296.

Wichterle, H., Lieberam, I., Porter, J., and Jessell, T. (2002). Directed differentiation of embryonic stem cells into motor neurons. Cell 110, 385.

Zhang, S. C., Wernig, M., Duncan, I. D., Brustle, O., and Thomson, J. A. (2001). In vitro differentiation of transplantable neural precursors from human embryonic stem cells. Nat Biotechnol 19, 1129-1133.

From the foregoing description, various modifications and changes in the compositions and methods will occur to those skilled in the art. All such modifications coming within the scope of the appended claims are intended to be included Each recited range includes all combinations and sub-combinations of ranges, as well as specific numerals contained therein.

All publications and patent documents cited above are hereby incorporated by reference in their entirety for all purposes to the same extent as if each were so individually denoted.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

What is claimed is:

1. A method of differentiating primate embryonic stem cells into a substantially pure homogeneous population of neural precursor cells comprising:
    (a) obtaining a primate embryonic stem cell culture,
    (b) propagating the stem cells on feeder cells one or more days to form embryonic stem cell clusters,
    (c) triturating the stem cell clusters
    (d) washing the triturated stem cell clusters at least once in a physiological medium,
    (e) forming the stem cell clusters into spheroid bodies in suspension medium by incubating the stem cell clusters in serum free medium supplemented with N2, B27, fibroblast growth factor 2, epithelial growth factor, and N-acetyl-cysteine, and
    (f) culturing the spheroid bodies in an expansion medium containing serum or a serum substitute, fibroblast growth factor 2, epithelial growth factor, and 2 mM N-acetyl-cysteine, wherein a substantially pure homogeneous population of neural precursor cells that is at least 90% pure is generated.

2. The method of claim 1, wherein the primate neural precursor cells are human neural precursor cells.

3. The method of claim 2, wherein the human neural precursor cells are multipotent.

4. The method of claim 1, wherein the embryonic stem cells are human embryonic cells.

5. The method of claim 4, wherein the human embryonic cells are undifferentiated.

6. The method of claim 1, wherein the resulting substantially pure homogeneous population of neural precursor cells is characterized by substantially reduced expression of Oct-4 or Nanog.

7. The method of claim 1, wherein the resulting substantially pure homogeneous population of neural precursor cells is characterized by being negative for the expression of GFAP, MAP2, GATA-1, GATA-4, Nkx2.5, PDX-1, Oct-4, Nanog, Brachyury/T, FoxA2, Sox17, AFP and O1.

8. The method of claim 1, wherein the resulting substantially pure homogeneous population of neural precursor cells is characterized by expression of at least one marker selected from the group consisting of Sox1, Sox2, Musashi-1, Nestin, Vimentin and Melk.

9. The method of claim 1, wherein the resulting substantially pure homogeneous population of neural precursor cells is able to generate neurons, astrocytes, and oligodendrocytes immediately after their generation from embryonic stem cells.

10. The method of claim 1, wherein the resulting substantially pure homogeneous population of neural precursor cells is able to generate neurons, astrocytes, and oligodendrocytes for at least 4 passages in vitro immediately after their generation from embryonic stem cells.

11. The method of claim 1, wherein the resulting substantially pure homogeneous population of neural precursor cells is at least 99% neural precursor cells.

12. The method of claim 1, wherein the resulting substantially pure homogeneous population of neural precursor cells is 100% neural precursor cells.

13. The method of claim 1, wherein the feeder cells are murine embryonic fibroblasts.

14. The method of claim 1, wherein the physiological medium is phosphate buffered saline.

15. The method of claim 1, wherein the fibroblast growth factor 2 and epithelial growth factor are at a final concentration of 20 ng/mL.

16. The method of claim 1, wherein the stem cell clusters in (e) are replated as monolayers in said expansion medium.

17. The method of claim 1, wherein no more than 10% of the neural precursor cells are negative for Vimentin.

18. The method of claim 1, wherein the resulting substantially pure homogeneous population of neural precursor cells has a reproducible proteome signature over at least 55 generations.

* * * * *